United States Patent [19]

Hirai et al.

[11] Patent Number: 4,621,150

[45] Date of Patent: Nov. 4, 1986

[54] CATALYST AND METHOD FOR ISOMERIZATION

[75] Inventors: Kenji Hirai; Takamasa Fuchikami, both of Sagamihara; Hiroaki Hirose, Ichihara, all of Japan; Iwao Ojima, Stony Brook, N.Y.

[73] Assignee: Sagami Chemical Research Center, Tokyo, Japan

[21] Appl. No.: 703,617

[22] Filed: Feb. 21, 1985

[30] Foreign Application Priority Data

Feb. 24, 1984 [JP] Japan .................................. 59-32513
Jul. 30, 1984 [JP] Japan ................................. 59-157594
Sep. 25, 1984 [JP] Japan ................................. 59-198717

[51] Int. Cl.$^4$ ............................................ C07C 69/76
[52] U.S. Cl. ........................................ 560/51; 560/53; 560/59; 560/60; 560/121; 560/126; 560/183; 502/112; 502/115; 549/430; 568/427; 568/592
[58] Field of Search ....................... 560/51, 53, 59, 60, 560/121, 126, 183; 568/427, 592; 549/430; 570/51; 502/112, 115

[56] References Cited

U.S. PATENT DOCUMENTS 3,959,349  5/1976  Kogure .................................. 560/51
4,016,196  4/1977  Kogure .................................. 560/51
4,042,617  8/1977  Kogure .................................. 560/51
4,316,046  2/1982  Costa .................................... 560/51

Primary Examiner—Paul J. Killos
Attorney, Agent, or Firm—Oblon, Fisher, Spivak, McClelland & Maier

[57] ABSTRACT

A catalyst for isomerization consisting essentially of a salt or complex salt represented by the formula:

$$[ML_m]^{n+}[Y]_n^- \quad (I)$$

where M is a metal of Group IB, IIA, IIB or VIII of the periodic table, L is a ligand, Y is a conjugated base of a Brønsted acid, m is 0, 1, 2, 3 or 4 and n is 1, 2 or 3.

9 Claims, No Drawings

CATALYST AND METHOD FOR ISOMERIZATION

The present invention relates to a catalyst for isomerization and a method for isomerizing a glycidate, a 2-hydroxy-3-butenoate or an ethylene oxide derivative in the presence of the catalyst.

There have been several reports on reagents for isomerizing glycidates. As reaction reagents for isomerization useful for the production of pyruvic acid derivatives, there have been known (a) an acid mixture of a lower fatty acid and a mineral acid such as hydrochloric acid or sulfuric acid (Japanese Examined Patent Publication No. 35069/1978 and Japanese Unexamined Patent Publication No. 149970/1978), and (b) a Lewis acid such as boron trifluoride or aluminum chloride, or a proton acid such as sulfuric acid or p-toluenesulfonic acid (Japanese Unexamined Patent Publication No. 99445/1981). However, the method of using the reagent (a) has a drawback that substantial amounts of aldehydes are likely to be produced as by-products due to decarboxylation, and the yield of the reaction is low. Whereas, the method of using the reagent (b) has a drawback that only corrosive sulfuric acid is practically useful as a catalyst, and in order to obtain a satisfactory yield with other members of the reagent, such members are required to be used in an amount at least equimolar to the substrate.

As reagents for isomerizing glycidates to 2-hydroxy-3-butenoates, there have been known (c) a proton acid such as sulfuric acid or hydrochloric acid (Japanese Examined Patent Publication No. 19093/1982), (d) a strongly acidic cation exchange resin (Japanese Examined Patent Publication No. 8869/1979), and (e) a Lewis acid such as boron trifluoride, aluminum chloride or magnesium chloride (Japanese Examined Patent Publication No. 19092/1982 and Japanese Unexamined Patent Publication No. 22613/1980). However, the method of using the reagent (c) has a drawback that an extraction operation is required for the separation of the proton acid used and the resulting product, and in certain cases, a silica gel column must be used for purification, whereby the yield is low. The method of using the reagent (d) has a drawback that an expensive ion exchange resin must be used in a great amount. In the case of the reagent (e), it is necessary to use a great amount of a Lewis acid in a special solvent, and the yield in the isomerization reaction is not good.

Further, a method is known wherein an arylpyruvate is obtained by treating a 2-hydroxy-3-aryl-3-butenoate with a base to transfer the double bond (Japanese Examined Patent Publication No. 35068/1978). However, this method has a drawback that it is not suitable for application to a substrate having a functional group weak to a base since it requires an equimolar amount of a metal alcoholate as the base, and the reaction must be conducted under a completely anhydrous condition.

An arylacetaldehyde, particularly phenylacetaldehyde, is useful as a starting material or base material for the preparation of perfumes, or as an intermediate for the preparation of agricultural chemicals or medicines. For the production of an arylacetaldehyde, there have been known (1) a method for producing phenylacetaldehyde by the dehydration reaction of styrene glycol, (2) a method for producing phenylacetaldehyde by the oxidation of β-phenylethyl alcohol, (3) a method for producing an arylacetaldehyde by the decomposition of an arylglycidic acid or an ester thereof. Phenylacetaldehyde is a very active compound and is likely to undergo changes due to e.g. oxidation or dehydration. Accordingly, the above conventional methods (1) to (3) are not suitable for practical industrial applications. Further, there have been known (4) a method for producing phenylacetaldehyde by the formylation of a benzylihalide with carbon monoxide and hydrogen in the presence of a catalyst (Japanese Examined Patent Publications No. 31128/1980 and No. 43455/1980, and Japanese Unexamined Patent Publications No. 113727/1981 and No. 93020/1984), and (5) a method for producing phenylacetaldehyde by the oxidation of styrene in the presence of a catalyst (Japanese Unexamined Patent Publications No. 35063/1980 and No. 91945/1982). However, these methods require considerable amounts of catalysts, and the yields and selectivity are low. Furthermore, in the method (4), a high pressure gas is employed and a special reaction apparatus is required. Thus, the method has difficulties in its industrial application. Phenylacetaldehyde is industrially produced, in most cases, by the isomerization of styrene oxide. As conventional methods for the production of phenylacetaldehyde by the isomerization of styrene oxide, there have been known (6) a method wherein the isomerization is thermally carried out (Japanese Unexamined Patent Publication No. 24234/1975), (7) a method wherein the isomerization is conducted in the presence of sulfuric acid or phosphoric acid (East German Patent No. 79285), and (8) a method wherein the isomerization is conducted in the presence of (a) a silica-alumina catalyst (Japanese Examined Patent Publication No. 3913/1977), (b) an alkaline earth metal sulfonate catalyst (Japanese Unexamined Patent Publication No. 106933/1975), (c) an acid clay catalyst (Japanese Examined Patent Publication No. 25932/1974) or (d) an acid-type ion exchange resin catalyst (Japanese Unexamined Patent Publication No. 18643/1982). However, the methods (6) and (8)-(a) to (c) have difficulties in the economical feasibility and the stability of the resulting phenylacetaldehyde as the reaction is conducted at a high temperature of at least 200° C. The method (7) has a difficulty in the treatment of the mineral acid used in a great amount. Further, method (8)-(d) has a drawback that in order to obtain the desired product in good yield, it is necessary to use the expensive ion exchange resin in a great amount. Thus, none of the conventional methods is fully satisfactory as an industrial method.

An arylacetaldehyde acetal is also useful as a starting material or base material for the preparation of perfumes, or as an intermediates for the production of agricultural chemicals or medicines. As a method for producing phenylacetaldehyde acetal by using styrene oxide as the starting material, there has been known a method wherein styrene oxide is thermally decomposed at a high temperature to phenylacetaldehyde, and then after an addition of an acid catalyst such as sulfuric acid or p-toluenesulfonic acid to the reaction system, the phenylacetaldehyde is reacted with an alcohol under a dehydration condition to produce phenylacetaldehyde acetal (Japanese Unexamined Patent Publication No. 24234/1975). However, this method has a drawback that the reaction temperature is high and the reaction time is long since the reaction is conducted under a dehydration condition.

The present inventors have conducted extensive researches with an aim to overcome the above-mentioned drawbacks inherent to the conventional methods, and as a result, have found an active catalyst which is capable of isomerizing a glycidate, a 2-hydroxy-3-butenoate or an ethylene oxide derivative in good yield, and which is capable of effectively catalyzing the reaction of an arylacetaldehyde with an alcohol to produce an arylacetaldehyde acetal. The present invention has been accomplished based on these discoveries.

Namely, the present invention provides a catalyst for isomerization consisting essentially of a salt or complex salt represented by the formula:

$$[ML_m]^{n+}[Y]_n^- \quad (I)$$

where M is a metal of Group IB, IIA, IIB or VIII of the periodic table, L is a ligand, Y is a conjugated base of a Brønsted acid, m is 0, 1, 2, 3 or 4 and n is 1, 2 or 3.

Further, the present invention provides a method for isomerizing a glycidate, a 2-hydroxy-3-butenoate or an ethylene oxide derivative, characterized in that the isomerization is conducted in the presence of the salt or complex salt of the formula I. Namely, the salt or complex salt of the formula I of the present invention may be employed for the isomerization and reaction as identified below.

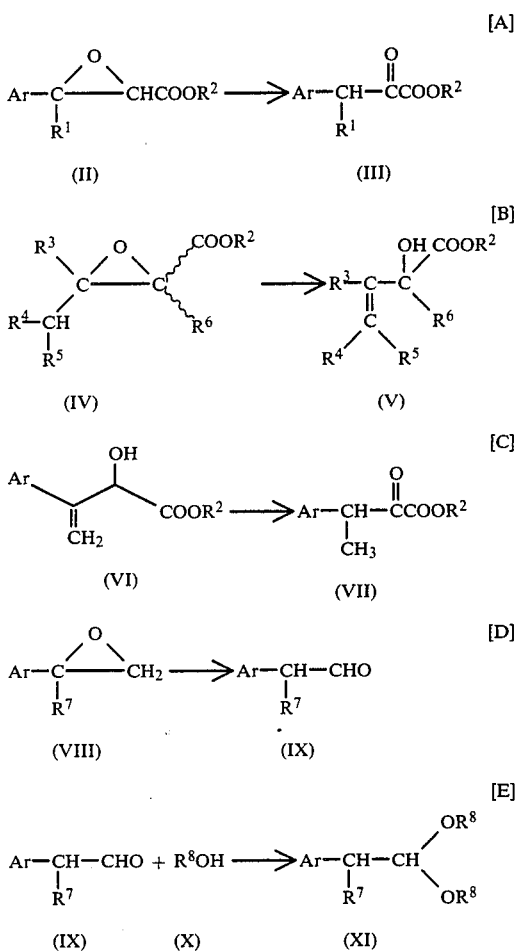

In the above formulas, Ar is an aryl group, $R^1$ is a hydrogen atom or a methyl group, $R^2$ is a lower alkyl group, each of $R^3$, $R^4$, $R^5$ and $R^6$ is a hydrogen atom, an alkyl group, an aralkyl group or an aryl group, or $R^3$ and $R^4$, $R^3$ and $R^6$, $R^4$ and $R^5$ or $R^4$ and $R^6$ may together form a polymethylene group, $R^7$ is a hydrogen atom or a lower alkyl group, and $R^8$ is an alkyl group, provided that two $R^8$ in the formula XI may together form a substituted or unsubstituted ethylene or polymethylene group.

Now, the present invention will be described in detail with reference to the preferred embodiments.

The salt or complex salt of the formula I of the present invention may be available as a commercial product, or may readily be prepared.

As the metal represented by M in the formula I, there may be mentioned, for example, copper, silver, magnesium, barium, calcium, zinc, cadmium, mercury, iron, cobalt, nickel, rhodium, palladium, iridium or platinum.

As the ligand represented by L, there may be mentioned, for example, a π-allyl group, a π-crotyl group, a π-methallyl group, a cyclopentadienyl group, an acetylacetonate group, a 8-methoxy-4-cycloocten-1-yl group, 1,5-cyclooctadiene, cyclooctatetraene, norbornadiene, dicyclopentadiene, benzene, pyridine or bipyridine, triphenylphosphine, triethylphosphine, tri-n-butylphosphine, tricyclohexylphosphine, triphenylphosphite, trimethylphosphite, triethylphosphite or tri-n-butylphosphite.

As the conjugated base of a Brønsted acid represented by Y, there may be mentioned a perhalogenoate such as a perchlorate or a periodate, or an conjugated base of an oxoacid such as a sulfonate, e.g. a trifluoromethanesulfonate, a fluorosulfonate, a trifluoromethylbenzenesulfonate or a methanesulfonate.

More specifically, the salt or complex salt of the formula I includes allyl(1,5-cyclooctadiene)palladium trifluoromethanesulfonate, allyl(1,5-cyclooctadiene)palladium perchlorate, allyl(1,5-cyclooctadiene)palladium p-trifluoromethylbenzenesulfonate, allyl(norbornadiene)palladium trifluoromethanesulfonate, allyl(norbornadiene)palladium perchlorate, allyl(norbornadiene)palladium p-trifluoromethylbenzenesulfonate, allyl(dicyclopentadiene)palladium trifluoromethanesulfonate, crotyl(1,5-cyclooctadiene)palladium trifluoromethanesulfonate, 8-methoxy-4-cyclocten-1-yl(1,5-cyclooctadiene)palladium trifluoromethanesulfonate, 8-methoxy-4-cycloocten-1-yl-(1,5-cyclooctadiene)palladium perchlorate, acetylacetonate(1,5-cyclooctadiene)palladium trifluoromethanesulfonate, acetylacetonate(norbornadiene)palladium trifluoromethanesulfonate, allyl bis(triphenylphosphine)palladium trifluoromethanesulfonate, allyl bis(triethylphosphine)palladium perchlorate, allyl bis(triethylphosphine)palladium trifluoromethanesulfonate, allyl bis(tri-n-butylphosphine)palladium perchlorate, allyl bis(tri-n-butylphosphine)palladium trifluoromethanesulfonate, allyl bis(triphenylphosphite)palladium perchlorate, allyl bis(triphenylphosphite)palladium trifluoromethanesulfonate, allyl bis(tri-ethylphosphite)palladium perchlorate, allyl bis(triethylphosphite)palladium trifluoromethanesulfonate, methallyl bis(triphenylphosphite)palladium perchlorate, 1,5-cyclooctadiene rhodium trifluoromethanesulfonate, norbornadiene rhodium trifluoromethanesulfonate, bis(1,5-cyclooctadiene)rhodium perchlorate, 1,5-cyclooctadiene(norbornadiene)rhodium trifluoromethanesulfonate, norbornadiene(1,5-cyclooctadiene)rhodium perchlorate, (1,5-cyclooctadiene)bis(triphenylphosphine)rhodium trifluoromethanesulfonate, (norbornadiene)bis(triphenylphosphine)rhodium perchlorate, (1,5-cyclooctadiene)bis(triphenylphosphite)rhodium perchlorate, (1,5-cyclooctadiene)bis(triphenylphosphite)rhodium trifluoromethanesulfonate, (1,5-cyclooctadiene)bis(triethylphosphite)rhodium trifluoromethanesulfonate, (1,5-cyclooctadiene)bis(triethylphosphite)rhodium perchlorate, bis(cyclopentadienyl)cobalt perchlorate, cyclopentadienyl(1,5-cyclooctadiene)nickel trifluoromethanesulfonate, nickel perchlorate, bypyridine(1,5-cyclooctadiene)iridium trifluoromethanesulfonate, 2,5-cyclopentadionate(1,5-cyclooctadiene)platinum trifluoromethanesulfonate, bis(bipyridine)platinum perchlorate, iron perchlorate, silver perchlorate, silver trifluoromethanesulfonate, silver p-trifluoromethylbenzenesulfonate, magnesium perchlorate, zinc perchlorate, barium perchlorate, calcium perchlorate, cadmium perchlorate and mercury perchlorate.

Further, as the conjugated base of a Bronsted acid represented by Y in the formula I, there may be employed a fluorinated polymer having a sulfonate as its side chain.

Now, the isomerization reactions wherein the salt or complex salt of the formula I is used, will be described.

(A) Production of an arylpyruvate by the isomerization of an arylglycidate

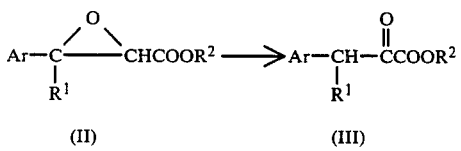

where Ar is an aryl group, $R^1$ is a hydrogen atom or a methyl group, and $R^2$ is a lower alkyl group.

As the arylglycidate represented by the formula II to be used in the above isomerization, there may be employed methyl esters of arylglycidic acids such as methyl 3-phenylglycidate, methyl 3-(4-methylphenyl)glycidate, methyl 3-(4-ethylphenyl)glycidate, methyl 3-(4-isopropylphenyl)glycidate, methyl 3-(4-t-butylphenyl)glycidate, methyl 3-(4-cyclohexylphenyl)glycidate, methyl 3-(3,4-dimethylphenyl)glycidate, methyl 3-(2,5-dimethylphenyl)glycidate, methyl 3-(4-fluorophenyl)glycidate, methyl 3-(4-chlorophenyl)glycidate, methyl 3-(4-bromophenyl)glycidate, methyl 3-(2-chlorophenyl)glycidate, methyl 3-(3-chlorophenyl)glycidate, methyl 3-(pentafluorophenyl)glycidate, methyl 3-(4-nitrophenyl)glycidate, methyl 3-(3-nitrophenyl)glycidate, methyl 3-(2-nitrophenyl)glycidate, methyl 3-(4-dimethylaminophenyl)glycidate, methyl 3-(2-methoxyphenyl)glycidate, methyl 3-(3-methoxyphenyl)glycidate, methyl 3-(4-methoxyphenyl)glycidate, methyl 3-(3,4-dimethoxyphenyl)glycidate, methyl 3-(4-benzyloxyphenyl)glycidate, methyl 3-(3-benzyloxyphenyl)glycidate, methyl 3-(4-methoxycarbonylphenyl)glycidate, methyl 3-(1-naphthyl)glycidate, methyl 3-(2-naphthyl)glycidate, and methyl 3-[4-(1-oxo-2-isoindolinyl)phenyl]glycidate, and lower alkyl esters such as ethyl esters, isopropyl esters or t-butyl esters of such acids. Further, as a glycidate with the β-position substituted by two substituents, there may be employed methyl esters of glycidic acids having an aromatic substituent, such as methyl 3-methyl-3-phenylglycidate, methyl 3-methyl-3-(4-methylphenyl)glycidate, methyl 3-methyl-3-(3-methylphenyl)glycidate, methyl 3-methyl-3-(2-methylphenyl)glycidate, methyl 3-methyl-3-(4-ethylphenyl)glycidate, methyl 3-methyl-3-(4-isopropylphenyl)glycidate, methyl 3-methyl-3-(4-isobutylphenyl)glycidate, methyl 3-methyl-3-(4-t-butylphenyl)glycidate, methyl 3-methyl-3-(4-cyclohexylphenyl)glycidate, methyl 3-methyl-3-(4-chlorophenyl)glycidate, methyl 3-methyl-3-(4-fluorophenyl)glycidate, methyl 3-methyl-3-(4-methoxyphenyl)glycidate, methyl 3-methyl-3-(4-acetoxyphenyl)glycidate, methyl 3-methyl-3-(3,4-dimethylphenyl)glycidate, methyl 3-methyl-3-(2,5-dimethylphenyl)glycidate, methyl 3-methyl-3-[4-(4'-fluorophenyl)phenyl]glycidate, methyl 3-methyl-3-(4-benzyloxyphenyl)glycidate, methyl 3-methyl-3-(3-benzyloxyphenyl)glycidate, methyl 3-methyl-3-(4-phenoxyphenyl)glycidate, methyl 3-methyl-3-(3-phenoxyphenyl)glycidate, methyl 3-methyl-3-[4-(1-oxo-2-isoindolinyl)phenyl]glycidate, methyl 3-methyl-3-(4-dimethylaminophenyl)glycidate, methyl 3-methyl-3-(2-methylphenyl)glycidate, methyl 3-methyl-3-(4-methoxycarbonylphenyl)glycidate, methyl 3-methyl-3-naphthylglycidate and methyl 3-methyl-3-indolinylglycidate, and lower alkyl esters such as ethyl esters, isopropyl esters or t-butyl esters of such acids.

Such a substituted glycidate represented by the formula II is a compound which is readily obtainable by a so-called Darzens' reaction from a carbonyl compound and a 2-haloacetate. Further, this compound may also be produced by an epoxidation reaction of an α,β-unsaturated carboxylate.

For the isomerization reaction, the catalyst for isomerization represented by the formula I may be used within a range of from 0.01 to 10 mol % relative to the arylglycidate of the formula II as the starting material. However, from the viewpoints of the economy and the catalytic activity, it is preferred to use the catalyst in an amount within a range of from 0.1 to 1.0 mol %.

The method of the present invention may be conducted without using a solvent. However, it is possible to use a solvent which does not affect the reaction, for example, an aromatic hydrocarbon solvent such as benzene, toluene or xylene, a halogenated solvent such as chloroform or methylene chloride, a ketone solvent such as acetone, methyl ethyl ketone or diethyl ketone, or other solvents such as ethyl acetate, dimethylsulfoxide, dimethylformamide or diisopropyl ether.

The reaction proceeds smoothly within a range of from room temperature to 200° C. However, from the viewpoints of e.g. the efficiency of the reaction and the selectivity, it is preferred to conduct the reaction at a temperature of from 40° to 160° C.

Among the arylpyruvates obtainable by the isomerization of the present invention, e.g. phenylpyruvate is known to be a compound which can readily be converted to phenylalanine as a starting material for a methyl ester of L-aspartyl-L-phenylalanine which is useful as a sweetner.

Further, a 3-methyl-2-ketocarboxylate obtainable by the above-mentioned isomerization can readily be led, by treatment with a suitable oxidizing agent, to a 2-aryl propionic acid derivative useful as a anti-inflammatory drug.

(B) Production of a 2-hdyroxy-3-alkenoate by the isomerization of a glycidate

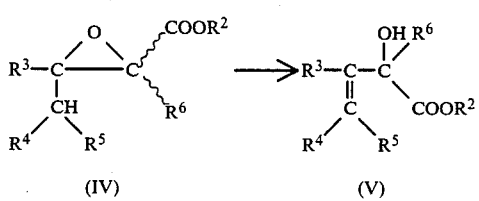

where each of $R^3$, $R^4$, $R^5$ and $R^6$ is a hydrogen atom, an alkyl group, an aralkyl group or an aryl group, or $R^3$ and $R^4$, $R^3$ and $R^6$, $R^4$ and $R^5$ or $R^4$ and $R^6$ may together form a polymethylene group, and $R^2$ is a lower alkyl group.

The glycidates represented by the formula IV to be used for the above isomerization, there may be employed methyl esters of glycidic acids having an aromatic substituent, such as methyl 3-methyl-3-phenylglycidate, methyl 3-ethyl-3-phenylglycidate, methyl 3-isopropyl-3-phenylglycidate, methyl 3-isobutyl-3-phenylglycidate, methyl 3-hexyl-3-phenylglycidate, methyl 3-octyl-3-phenylglycidate, methyl 3-methoxymethyl-3-phenylglycidate, methyl 3-methyl-3-(4-methylphenyl)glycidate, methyl 3-methyl-3-(3-methylphenyl)glycidate, methyl 3-methyl-3-(2-methylphenyl)glycidate, methyl 3-methyl-3-(4-ethylphenyl)glycidate, methyl 3-methyl-3-(4-isopropylphenyl)glycidate, methyl 3-methyl-3-(4-isobutylphenyl)glycidate, methyl 3-methyl-3-(4-t-butylphenyl)glycidate, methyl 3-methyl-3-(4-t-cyclohexylphenyl)glycidate, methyl 3-methyl-3-(4-chlorophenyl)glycidate, methyl 3-methyl-3-(4-fluorophenyl)glycidate, methyl 3-methyl-3-(4-methoxyphenyl)glycidate, methyl 3-methyl-3-(4-acetoxyphenyl)glycidate, methyl 3-methyl-3-(3,4-dimethylphenyl)glycidate, methyl 3-methyl-3-(2,5-dimethylphenyl)glycidate, methyl 3-methyl-3-[4-(4'-fluorophenyl)phenyl]glycidate, methyl 3-methyl-3-(4-benzyloxyphenyl)glycidate, methyl 3-methyl-3-(3-benzyloxyphenyl)glycidate, methyl 3-methyl-3-(4-phenoxyphenyl)glycidate, methyl 3-methyl-3-(3-phenoxyphenyl)glycidate, methyl 3-methyl-3-[4-(1-oxo-2-isoindolinyl)phenyl]glycidate, methyl 3-methyl-3-(4-dimethylaminophenyl)glycidate, methyl 3-methyl-3-(2-methylphenyl)glycidate, methyl 3-methyl-3-(4-methoxycarbonylphenyl)glycidate, methyl 3-ethyl-3-(4-methylphenyl)glycidate, methyl 3-ethyl-3-(4-fluorophenyl)glycidate, methyl 3-ethyl-3-(4-methoxycarbonylphenyl)glycidate, methyl 3-isopropyl-3-(4-methylphenyl)glycidate, methyl 3-isopropyl-3-(4-chlorophenyl)glycidate, methyl 3-butyl-3-(4-methylphenyl)glycidate, methyl 3-methyl-3-naphthylglycidate, methyl 3-methyl-3-indolinylglycidate, methyl 2,3-dimethyl-3-phenylglycidate, methyl 2,3-diethyl-3-phenylglycidate, methyl 2-methyl-3-ethyl-3-phenylglycidate, methyl 2-ethyl-3-methyl-3-(4-methylphenyl)glycidate, methyl 2-phenyl-3-methyl-3-phenylglycidate, methyl 2-octyl-3-methyl-3-phenylglycidate, methyl 2-methyl-3-octyl-3-phenylglycidate and methyl 3-benzylglycidate, or ethyl esters, isopropyl esters, or t-butyl esters of such acids. Further, as a glycidate having an alkyl substituent, there may be employed methyl esters of glycidic acids such as methyl 3-methylglycidate, methyl 3-ethylglycidate, methyl 3-isopropylglycidate, methyl 3-octylglycidate, methyl 3-cyclohexylglycidate, methyl 3-methoxymethylglycidate, methyl 3,3-dimethylglycidate, methyl 3,3-diethylglycidate, methyl 3-methyl-3-ethylglycidate, methyl 3-methyl-3-isopropylglycidate, methyl 3-methyl-3-butylglycidate, methyl 3-methyl-3-octylglycidate, methyl 3-methoxymethyl-3-methylglycidate, methyl 3-acetoxymethyl-3-methylglycidate, methyl 2,3-dimethylglycidate, methyl 2-methyl-3-ethylglycidate, methyl 2,3-epoxycyclohexylidene acetate, methyl 2,3-epoxycyclopentylidene acetate, methyl 2,3-epoxycyclododecylidene acetate, methyl 2-methyl-2,3-epoxycyclohexylidene acetate, methyl 2-methyl-2,3-epoxycyclopentylidene acetate, methyl 2-(4-fluorophenyl)-2,3-epoxycyclohexylidene acetate, methyl 2-phenyl-2,3-epoxycyclohexylidene acetate, methyl 3,3-dimethyl-2-phenylglycidate, methyl 3,3-diethyl-2-phenylglycidate, 1-methoxycarbonyl-1-cyclohexeneoxide and 1-methoxycarbonyl-2-methyl-1-cyclohexeneoxide, and lower alkyl esters of the above glycidic acids, such as the ethyl esters, isopropyl esters or t-butyl esters.

The above-mentioned substituted glycidate represented by the formula IV is a compound which is readily obtainable by a so-called Darzens' reaction from a carbonyl compound and a 2-halocarboxylate. Further, this compound may also be prepared by e.g. the epoxidation reaction of an $\alpha,\beta$-unsaturated carboxylate.

In the practical operation of the isomerization, the catalyst for isomerization represented by the formula I is used in an amount within a range of from 0.001 to 10 mol % relative to the substituted glycidate of the formula IV as the starting material.

The method of the present invention may be conducted without using a solvent. However, it is possible to use a solvent which does not affect the reaction, for instance, an aromatic hydrocarbon solvent such as benzene, toluene or xylene, a halogenated solvent such as methylene chloride, chloroform or carbon tetrachloride, an ether solvent such as diethyl ether, diisopropyl ether or dimethoxy ethane, an aliphatic hydrocarbon solvent such as pentane or hexane, an ester or ketone solvent such as ethyl acetate, acetone, methyl ethyl ketone or methyl isopropyl ketone, or other solvent such as dimethylsulfoxide or dimethylformamide.

The reaction may be conducted at a temperature of from room temperature to 160° C. In the case where a glycidate of the formula IV where $R^3$ is an aryl group and each of $R^4$, $R^5$ and $R^6$ is a hydrogen atom, is employed, compounds other than the desired compound (3-methylpyruvate) are likely to form as by-products at a high temperature. Accordingly, for the production of a 2-hydroxy-3-alkenoate, it is preferred, from the viewpoint of the selectivity of the reaction, to choose a temperature range from room temperature to 100° C.

Among 2-hydroxy carboxylic acid derivatives obtainable by the reaction of the present invention, 3-(substituted aryl)alkenoates can be further isomerized to obtain substituted arylpyruvates. They may be converted by the treatment with a suitable oxidizing agent, to 2-(substituted aryl)propionic acid compounds useful as anti-inflammatory drugs (see Reference Example given hereinafter).

Further, among 2-hydroxy carboxylate derivatives represented by the formula V in the present reaction, e.g. isopropenyl lactate can be converted to isopropenyl lactic acid, which is useful as a monomer for the copolyemrization with e.g. acrylic acid (West German Patent Publication No. 2646803), and also useful as a starting material for an oxazolidine dione derivative having an insecticidal activity (West German Patent Publication No. 2207576).

(C) Production of a pyruvate by the isomerization of a 2-hydroxy-3-butenoate

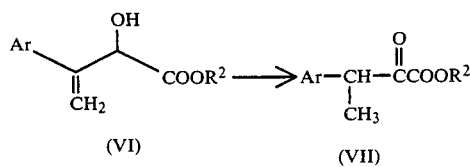

where Ar is an aryl group, and $R^2$ is a lower alkyl group.

As the 2-hydroxy-3-butenoate represented by the formula VI to be used for the isomerization, there may be employed methyl esters of 2-hydroxy-3-butenoic acids, such as methyl 2-hydroxy-3-phenyl-3-butenoate, methyl 2-hydroxy-3-(4-methylphenyl)-3-butenoate, methyl 2-hydroxy-3-(4-ethylphenyl)-3-butenoate, methyl 2-hydroxy-3-(4-isobutylphenyl)-3-butenoate, methyl 2-hydroxy-3-(4-cyclohexylphenyl)-3-butenoate, methyl 2-hydroxy-3-(4-methoxyphenyl)-3-butenoate, methyl 2-hydroxy-3-(4-phenoxyphenyl)-3-butenoate, methyl 2-hydroxy-3-(3-phenoxyphenyl)-3-butenoate, methyl 2-hydroxy-3-(4-biphenylyl)-3-butenoate, methyl 2-hydroxy-3-(4-chlorophenyl)-3-butenoate, methyl 2-hydroxy-3-(4-fluorophenyl)-3-butenoate, methyl 2-hydroxy-3-(biphenylyl)-3-butenoate, methyl 2-hydroxy-3-(2-naphthyl)-3-butenoate and methyl 2-hydroxy-3-(6-methoxy-2-naphthyl)-3-butenoate, and their lower alkyl esters such as ethyl esters or isopropyl esters instead of the methyl esters.

The 2-hydroxy-3-butenoate represented by the formula VI as a starting material of this method, may be obtained by the isomerization reaction of a 3-methylglycidate as the starting material of the method (B) (Japanese Examined Patent Publications No. 3506/1978, No. 8669/1979, No. 8667/1979, No. 19093/1982 and No. 19092/1982).

In the practical operation of the isomerization, the catalyst for isomerization represented by the formula I, is used in an amount within a range of from 0.01 to 10 mol % relative to the 2-hydroxy-3-butenoate represented by the formula VI as the starting material. However, it is preferred to use the catalyst in an amount of from 0.1 to 1.0 mol % in view of the efficiency of the reaction and the catalytic activity.

This method may be conducted in the absence of a solvent. However, it is possible to use a solvent which does not affect the reaction, for example, an aromatic hydrocarbon solvent such as toluene or xylene, or other solvents such as diisopropyl ether, dimethylsulfoxide or dimethylformamide.

The reaction proceeds at a temperature of from room temperature to 200° C. However, it is preferred to conduct the reaction at a temperature of from 100 to 160° C. from the viewpoints of e.g. the efficiency of the reaction.

The 2-ketocarboxylate obtainable by this reaction, can readily be led, by treatment with a suitable oxidizing agent, to a 2-arylpropionic acid derivative, which is useful as an anti-inflammatory drug (see the Reference Example given hereinafter).

(D) Production of an arylacetaldehyde by the isomerization of an ethylene oxide derivative

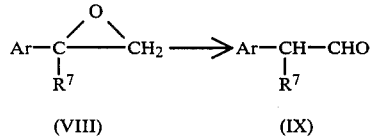

where Ar is an aryl group, and $R^7$ is a hydrogen atom or a lower alkyl group.

The ethylene oxide derivative of the formula VIII as the starting material of this method is a compound which is industrially readily available, or a compound which can be easily synthesized from a starting material which is industrially readily available. For instance, it can be easily synthesized from an acetophenone by halogenation, reduction and epoxidation.

More specifically, there may be mentioned unsubstituted arylethylene oxides such as styrene oxide or β-naphthyl ethylene oxide, or substituted arylethylene oxides such as o-methylstyrene oxide, m-methylstyrene oxide, p-methylstyrene oxide, m,p-dimethylstyrene oxide, p-ethylstyrene oxide, p-cyclohexylstyrene oxide, p-isobutylstyrene oxide, m-fluorostyrene oxide, p-fluorostyrene oxide, p-chlorostyrene oxide, p-bromostyrene oxide, p-methoxystyrene oxide, m,p-dimethoxystyrene oxide, 2-phenylpropylene oxide, 2-phenyl-1-butene oxide, 2-(p-methylphenyl)propylene oxide, 2-(p-fluorophenyl)propylene oxide and β-(6-methoxynaphthyl)ethylene oxide.

For this method, the amount of the salt or complex salt of the formula I is not critical. It is usually employed in an amount within a range of from 0.01 to 10 mol % relative to the ethylene oxide derivative of the formula VIII. However, it is preferred to use it in an amount within the range of from 0.1 to 1.0 mol % from the viewpoints of the economy and the catalytic activity.

The reaction is usually conducted in a solvent, but may be conducted in a solventless system or in a vapour phase system. When the reaction is conducted in a solvent, there may be employed, as such a solvent, an aromatic hydrocarbon such as benzene, toluene, xylene or mesitylene, an aliphatic hydrocarbon such as n-hexane, n-pentane or cyclohexane, a halogenated hydrocarbon such as chloroform or methylene chloride, or an ether solvent such as tetrahydrofuran or dioxane. The reaction proceeds smoothly within a temperature range of from 0° to 200° C. However, it is preferred to conduct the reaction at a temperature within a range of from room temperatue to about 100° C., from the viewpoints of the efficiency of the reaction, the selectivity and the stability of the resulting arylacetaldehyde.

(E) Production of an arylacetaldehyde acetal by the reaction of an arylacetaldehyde with an alcohol

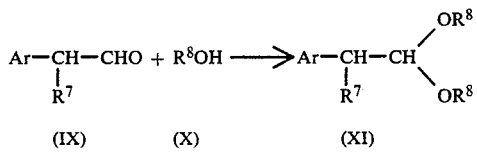

where Ar is an aryl group, $R^7$ is a hydrogen atom or a lower alkyl group, and $R^8$ is an alkyl group, provided that two $R^8$ in the formula XI may together form a substituted or unsubstituted ethylene or polymethylene group.

In this process, the acrylacetaldehyde prepared in the above method (D) is reacted with an alcohol of the formula X in the presence of the salt or complex salt of the formula I to form an arylacetaldehyde acetal of the formula XI.

As the alcohol which may be employed in this process, there may be mentioned an alcohol such as methanol, ethanol, propanol or butanol, a glycol such as ethylene glycol, trimethylene glycol, styrene glycol, 1,2-propanediol, 2,3-butandiol or 2-methyl-1,3-propanediol, or glycerol.

In this process, the aldehyde prepared in the previous step may be employed after being isolated. However, it may not necessarily be isolated, and it is possible to convert the crude reaction product to an arylacetaldehyde acetal by adding to the crude reaction product a desired alcohol. The reaction condition of this process may the same as the condition of the previous step (D).

Now, the present invention will be described in further detail with reference to Examples. However, it should be understood that the present invention is by no means restricted by these specific Examples.

In the following Examples and Reference Example, the following abbreviations were used.

| $\eta^3$-C$_3$H$_5$: | $\eta^3$-allyl group |
| --- | --- |
| MeO—C$_8$H$_{12}$: | 8-methoxy-4-cycloocten-1-yl group |
| COD: | 1,5-cyclooctadiene |
| NBD: | norbornadiene |
| Tf: | trifluoromethanesulfonate (CF$_3$SO$_3$) |
| Me: | methyl group |
| Et: | ethyl group |
| $^i$Pr: | isopropyl group |
| $^i$Bu: | isobutyl group |

EXAMPLE 1

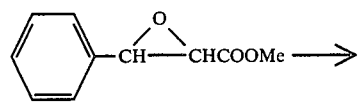 ⟶

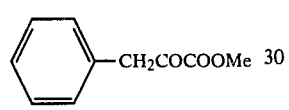

Methyl 3-phenylglycidate (1.78 g, 10 mmol), allyl(1,5-cyclooctadiene)palladium trifluoromethanesulfonate (40 mg, 0.10 mmol) as a catalyst and benzene (10 ml) as a solvent, were introduced into a 25 ml egg plant type flask and stirred at 60° C. for 1 hour. After the completion of the reaction, the reaction mixture was cooled to room temperature, and the solvent was distilled off under reduced pressure. Hexane (about 15 ml) and ether (about 5 ml) were added to the residue, and the precipitates were filtered and washed with hexane. From the filtrate and washing solution, the solvent was distilled off under reduced pressure, whereby colorless oily substance (1.75 g) was obtained. From the nuclear magnetic resonance spectrum and the infrared absorption spectrum, this substance was confirmed to be substantially pure methyl 3-phenylpyruvate. The results are shown in the following table.

(Example 1)

| Starting material: | 1.78 g (10 mmol) |
| --- | --- |
| Catalyst: | [($\eta^3$-C$_3$H$_5$)Pd(COD)][Tf], 40 mg (0.10 mmol) |
| Solvent: | Benzene (10 ml) |
| Reaction temp.: | 60° C. |
| Reaction time: | 1 hr. |
| Yield: | 98% |

EXAMPLES 2 AND 3

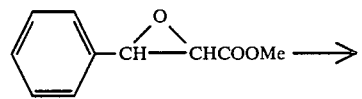 ⟶

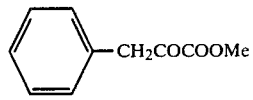

In the same manner as in Example 1, methyl 3-phenylpyruvate was obtained from methyl 3-phenylglycidate. The results are shown in the following tables.

(Example 2)

| Starting material: | 0.89 g (5.0 mmol) |
| --- | --- |
| Catalyst: | [Rh(COD)$_2$][Tf], 100 mg (0.20 mmol) |
| Solvent: | Benzene (10 ml) |
| Reaction temp.: | 80° C. |
| Reaction time: | 2 hrs. |
| Yield: | 98% |

(Example 3)

| Starting material: | 1.78 g (10 mmol) |
| --- | --- |
| Catalyst: | [(NBD)Rh(COD)][ClO$_4$], 8.0 mg (0.02 mmol) |
| Solvent: | Benzene (10 ml) |
| Reaction temp.: | 80° C. |
| Reaction time: | 2 hrs. |
| Yield: | 98% |

EXAMPLES 4 AND 5

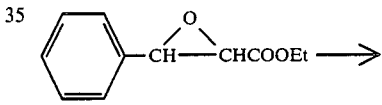 ⟶

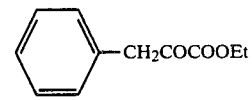

In the same manner as in Example 1, ethyl 3-phenylpyruvate was obtained from ethyl 3-phenylglycidate. The results are shown in the following tables.

(Example 4)

| Starting material: | 1.92 g (10 mmol) |
| --- | --- |
| Catalyst: | [($\eta^3$-C$_3$H$_5$)Pd(COD)][Tf], 40 mg (0.10 mmol) |
| Solvent: | Benzene (5 ml) |
| Reaction temp.: | 60° C. |
| Reaction time: | 1 hr. |
| Yield: | 100% |

(Example 5)

| Starting material: | 1.92 g (10 mmol) |
| --- | --- |
| Catalyst: | [($\eta^3$-C$_3$H$_5$)Pd(COD)][ClO$_4$], 36 mg (0.10 mmol) |
| Solvent: | Benzene (10 ml) |
| Reaction temp.: | 60° C. |
| Reaction time: | 1 hr. |
| Yield: | 95% |

EXAMPLES 6 TO 8

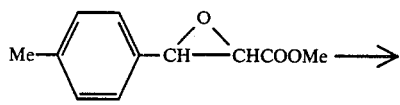

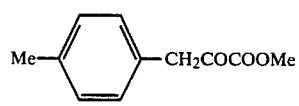

In the same manner as in Example 1, methyl 3-(4-methylphenyl)pyruvate was obtained from methyl 3-(4-methylphenyl)glycidate. The results are shown in the following tables.

(Example 6)

| | |
|---|---|
| Starting material: | 2.19 g (11 mmol) |
| Catalyst: | [($\eta^3$-C$_3$H$_5$)Pd(COD)][Tf], 40 mg (0.10 mmol) |
| Solvent: | Benzene (5 ml) |
| Reaction temp.: | 70° C. |
| Reaction time: | 2 hrs. |
| Yield: | 96% |

(Example 7)

| | |
|---|---|
| Starting material: | 1.92 g (10 mmol) |
| Catalyst: | [(MeO—C$_8$H$_{12}$)Pd(COD)][Tf], 5.0 mg (0.01 mmol) |
| Solvent: | Methylene chloride (10 ml) |
| Reaction temp.: | 50° C. |
| Reaction time: | 1 hr. |
| Yield: | 100% |

(Example 8)

| | |
|---|---|
| Starting material: | 0.50 g (2.6 mmol) |
| Catalyst: | [Ag][Tf], 2.0 mg (0.01 mmol) |
| Solvent: | Benzene (10 ml) |
| Reaction temp.: | Room temperature |
| Reaction time: | 2 hrs. |
| Yield: | 100% |

EXAMPLES 9 and 10

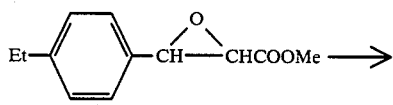

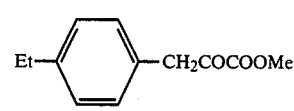

In the same manner as in Example 1, methyl 3-(4-ethylphenyl)pyruvate was obtained from methyl 3-(4-ethylphenyl)glycidate. The results are shown in the following tables.

(Example 9)

| | |
|---|---|
| Starting material: | 2.06 g (10 mmol) |
| Catalyst: | [($\eta^3$-C$_3$H$_5$)Pd(COD)][Tf], 40 mg (0.10 mmol) |
| Solvent: | Benzene (5 ml) |
| Reaction temp.: | 70° C. |
| Reaction time: | 2 hrs. |
| Yield: | 99% |

(Example 10)

| | |
|---|---|
| Starting material: | 2.06 g (10 mmol) |
| Catalyst: | [(MeO—C$_8$H$_{12}$)Pd(COD)][Tf], 30 mg (0.07 mmol) |
| Solvent: | Benzene (10 ml) |
| Reaction temp.: | 80° C. |
| Reaction time: | 2 hrs. |
| Yield: | 95% |

EXAMPLES 11 and 12

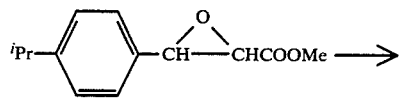

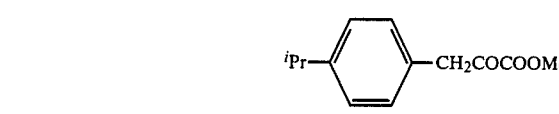

In the same manner as in Example 1, methyl 3-(4-isopropylphenyl)pyruvate was obtained from methyl 3-(4-isopropylphenyl)glycidate. The results are shown in the following tables.

(Example 11)

| | |
|---|---|
| Starting material: | 2.20 g (10 mmol) |
| Catalyst: | [($\eta^3$-C$_3$H$_5$)Pd(COD)][Tf], 40 mg (0.10 mmol) |
| Solvent: | Benzene (5 ml) |
| Reaction temp.: | 70° C. |
| Reaction time: | 1 hr. |
| Yield: | 99% |

(Example 12)

| | |
|---|---|
| Starting material: | 2.20 g (10 mmol) |
| Catalyst: | [(MeO—C$_8$H$_{12}$)Pd(COD)][Tf], 5.0 mg (0.01 mmol) |
| Solvent: | Methylene chloride (10 ml) |
| Reaction temp.: | 50° C. |
| Reaction time: | 2 hrs. |
| Yield: | 95% |

EXAMPLES 13 to 16

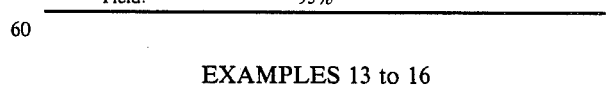

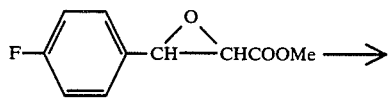

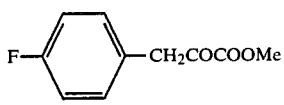

In the same manner as in Example 1, methyl 3-(4-fluorophenyl)pyruvate was obtained from methyl 3-(4-fluorophenyl)glycidate. The results are shown in the following tables.

(Example 13)

| Starting material: | 8.0 g (40 mmol) |
|---|---|
| Catalyst: | [(η³-C₃H₅)Pd(COD)][Tf], |
| | 130 mg (0.32 mmol) |
| Solvent: | Benzene (30 ml) |
| Reaction temp.: | 60° C. |
| Reaction time: | 2 hrs. |
| Yield: | 100% |

(Example 14)

| Starting material: | 1.96 g (10 mmol) |
|---|---|
| Catalyst: | [(η³-C₃H₅)Pd(COD)][Tf], |
| | 40 mg (0.10 mmol) |
| Solvent: | Benzene (10 ml) |
| Reaction temp.: | 60° C. |
| Reaction time: | 1 hr. |
| Yield: | 99% |

(Example 15)

| Starting material: | 2.00 g (10 mmol) |
|---|---|
| Catalyst: | [(MeO—C₈H₁₂)Pd(COD)][Tf], |
| | 5.0 mg (0.01 mmol) |
| Solvent: | Methylene chloride (10 ml) |
| Reaction temp.: | 50° C. |
| Reaction time: | 2 hrs. |
| Yield: | 98% |

(Example 16)

| Starting material: | 2.00 g (10 mmol) |
|---|---|
| Catalyst: | [Rh(COD)₂][Tf], |
| | 20 mg (0.04 mmol) |
| Solvent: | Benzene (10 ml) |
| Reaction temp.: | 80° C. |
| Reaction time: | 2 hrs. |
| Yield: | 100% |

EXAMPLES 17 and 18

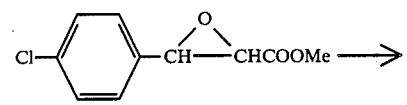

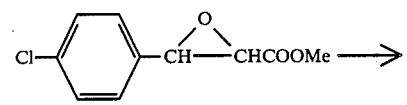

In the same manner as in Example 1, methyl 3-(4-chlorophenyl)pyruvate was obtained from methyl 3-(4-chlorophenyl)glycidate. The results are shown in the following tables.

(Example 17)

| Starting material: | 1.96 g (10 mmol) |
|---|---|
| Catalyst: | [(η³-C₃H₅)Pd(COD)][Tf], |
| | 40 mg (0.10 mmol) |
| Solvent: | Benzene (10 ml) |
| Reaction temp.: | 60° C. |
| Reaction time: | 2 hrs. |
| Yield: | 95% |

(Example 18)

| Starting material: | 1.96 g (10 mmol) |
|---|---|
| Catalyst: | [(η³-C₃H₅)Pd(COD)][ClO₄], |
| | 36 mg (0.10 mmol) |
| Solvent: | Benzene (10 ml) |
| Reaction temp.: | 80° C. |
| Reaction time: | 2 hrs. |
| Yield: | 92% |

EXAMPLES 19 and 20

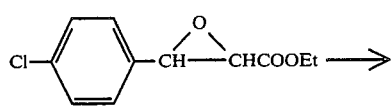

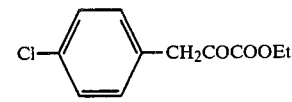

In the same manner as in Example 1, ethyl 3-(4-chlorophenyl)pyruvate was obtained from ethyl 3-(4-chlorophenyl)glycidate. The results are shown in the following tables.

(Example 19)

| Starting material: | 1.06 g (5.0 mmol) |
|---|---|
| Catalyst: | [(η³-C₃H₅)Pd(COD)][Tf], |
| | 40 mg (0.10 mmol) |
| Solvent: | Benzene (10 ml) |
| Reaction temp.: | 60° C. |
| Reaction time: | 2 hrs. |
| Yield: | 100% |

(Example 20)

| Starting material: | 1.50 g (7.1 mmol) |
|---|---|
| Catalyst: | [Rh(COD)₂][Tf], |
| | 10 mg (0.02 mmol) |
| Solvent: | Benzene (10 ml) |
| Reaction temp.: | 80° C. |
| Reaction time: | 2 hrs. |
| Yield: | 90% |

EXAMPLES 21 to 23

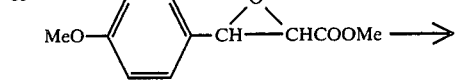

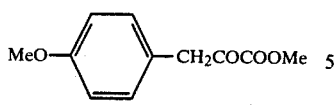

In the same manner as in Example 1, methyl 3-(4-methoxyphenyl)pyruvate was obtained from methyl 3-(4-methoxyphenyl)glycidate. The results are shown in the following tables.

(Example 21)

| Starting material: | 2.08 g (10 mmol) |
|---|---|
| Catalyst: | [(η³-C₃H₅)Pd(COD)][Tf], 40 mg (0.10 mmol) |
| Solvent: | Benzene (5 ml) |
| Reaction temp.: | 70° C. |
| Reaction time: | 2 hrs. |
| Yield: | 94% |

(Example 22)

| Starting material: | 2.08 g (10 mmol) |
|---|---|
| Catalyst: | [(MeO—C₈H₁₂)Pd(COD)][Tf], 5.0 mg (0.01 mmol) |
| Solvent: | Methylene chloride (10 ml) |
| Reaction temp.: | 50° C. |
| Reaction time: | 2 hrs. |
| Yield: | 100% |

(Example 23)

| Starting material: | 2.08 g (10 mmol) |
|---|---|
| Catalyst: | [(η³-C₃H₅)Pd(COD)][ClO₄], 3.6 mg (0.01 mmol) |
| Solvent: | Benzene (10 ml) |
| Reaction temp.: | 70° C. |
| Reaction time: | 2 hrs. |
| Yield: | 96% |

EXAMPLE 24

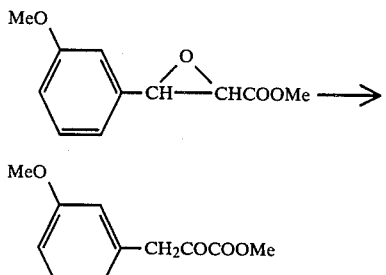

In the same manner as in Example 1, methyl 3-(3-methoxyphenyl)pyruvate was obtained from methyl 3-(3-methoxyphenyl)glycidate. The results are shown in the following table.

(Example 24)

| Starting material: | 1.30 g (6.3 mmol) |
|---|---|
| Catalyst: | [(η³-C₃H₅)Pd(COD)][Tf], 40 mg (0.10 mmol) |
| Solvent: | Benzene (5 ml) |
| Reaction temp.: | 70° C. |
| Reaction time: | 2 hrs. |
| Yield: | 100% |

EXAMPLE 25

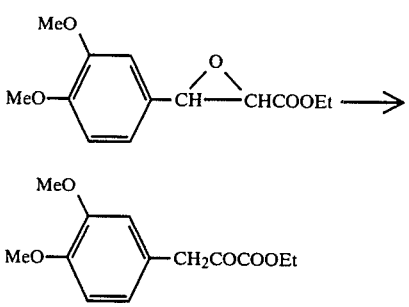

In the same manner as in Example 1, ethyl 3-(3,4-dimethoxyphenyl)pyruvate was obtained from ethyl 3-(3,4-dimethoxyphenyl)glycidate. The results are shown in the following table.

(Example 25)

| Starting material: | 2.52 g (10 mmol) |
|---|---|
| Catalyst: | [(η³-C₃H₅)Pd(COD)][Tf], 40 mg (0.10 mmol) |
| Solvent: | Benzene (10 ml) |
| Reaction temp.: | 70° C. |
| Reaction time: | 2 hrs. |
| Yield: | 95% |

EXAMPLE 26

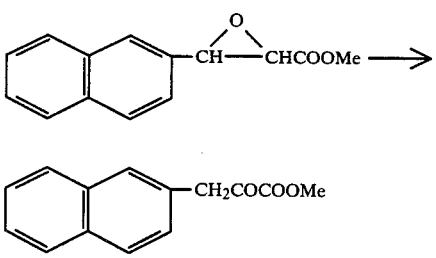

In the same manner as in Example 1, methyl 3-(2-naphthyl)pyruvate was obtained from methyl 3-(2-naphthyl)glycidate. The results are shown in the following table.

(Example 26)

| Starting material: | 2.28 g (10 mmol) |
|---|---|
| Catalyst: | [(η³-C₃H₅)Pd(COD)][Tf], 40 mg (0.10 mmol) |
| Solvent: | Benzene (15 ml) |
| Reaction temp.: | 80° C. |
| Reaction time: | 2 hrs. |
| Yield: | 93% |

EXAMPLE 27

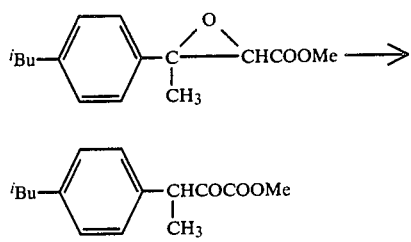

Methyl 3-methyl-3-(4-isobutylphenyl)glycidate (2.48 g, 10 mmol), allyl(1,5-cyclooctadiene)palladium trifluoromethanesulfonate (40 mg, 0.1 mmol) as a catalyst and toluene (15 ml) as a solvent, were introduced into a 50 ml egg plant type flask, and stirred for 3 hours under reflux. After cooling the reaction mixture, the solvent was distilled off under reduced pressure. Hexane and ether were added to the residue, and the precipitates were filtered off. The solvent was completely removed from the filtrate, whereby 2.36 g of oily substance was obtained. From the nuclear magnetic resonance spectrum and the infrared absorption spectrum, this substance was found to be substantially pure methyl 3-methyl-3-(4-isobutylphenyl)pyruvate. The results are shown in the following table.

(Example 27)

| | |
|---|---|
| Starting material: | 2.48 g (10 mmol) |
| Catalyst: | [($\eta^3$-C$_3$H$_5$)Pd(COD)][Tf], 40 mg (0.10 mmol) |
| Solvent: | Benzene (15 ml) |
| Reaction temp.: | 110° C. |
| Reaction time: | 3 hrs. |
| Yield: | 95% |

EXAMPLE 28

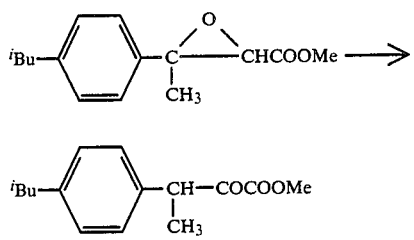

By using zinc perchlorate as a catalyst, in the same manner as in Example 27, methyl 3-methyl-3-(4-isobutylphenyl)pyruvate was obtained from methyl 3-methyl-3-(4-isobutylphenyl)glycidate. The results are shown in the following table.

(Example 28)

| | |
|---|---|
| Starting material: | 2.48 g (10 mmol) |
| Catalyst: | [Zn][ClO$_4$]$_2$, 26 mg (0.10 mmol) |
| Solvent: | Toluene (15 ml) |
| Reaction temp.: | 110° C. |
| Reaction time: | 3 hrs. |
| Yield: | 80% |

EXAMPLE 29

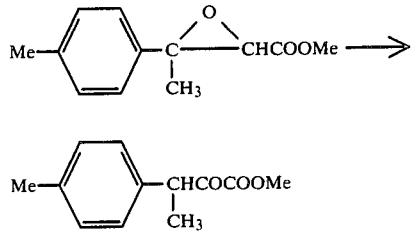

Methyl 3-methyl-3-(4-methylphenyl)glycidate was isomerized in the same manner as in Example 27, whereby methyl 3-methyl-3-(4-methylphenyl)pyruvate was obtained. The results are shown in the following table.

(Example 29)

| | |
|---|---|
| Starting material: | 2.06 g (10 mmol) |
| Catalyst: | [($\eta^3$-C$_3$H$_5$)Pd(COD)][Tf], 40 mg (0.10 mmol) |
| Solvent: | Toluene (10 ml) |
| Reaction temp.: | 110° C. |
| Reaction time: | 3 hrs. |
| Yield: | 100% |

EXAMPLES 30 and 31

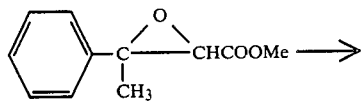

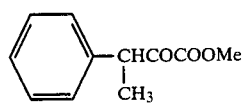

Methyl 3-methyl-3-phenylglycidate was isomerized in the same manner as in Example 27, whereby methyl 3-methyl-3-phenylpyruvate was obtained. The results are shown in the following tables.

(Example 30)

| | |
|---|---|
| Starting material: | 1.92 g (10 mmol) |
| Catalyst: | [($\eta^3$-C$_3$H$_5$)Pd(COD)][Tf], 40 mg (0.10 mmol) |
| Solvent: | Toluene (15 ml) |
| Reaction temp.: | 110° C. |
| Reaction time: | 2 hrs. |
| Yield: | 95% |

(Example 31)

| | |
|---|---|
| Starting material: | 1.92 g (10 mmol) |
| Catalyst: | [Zn][ClO$_4$]$_2$, 26 mg (0.10 mmol) |
| Solvent: | Toluene (15 ml) |
| Reaction temp.: | 120° C. |
| Reaction time: | 5 hrs. |
| Yield: | 90% |

EXAMPLES 32 to 34

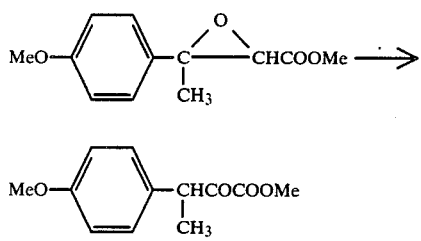

Methyl 3-methyl-3-(4-methoxyphenyl)glycidate was isomerized in the same manner as in Example 27, whereby methyl 3-methyl-3-(4-methoxyphenyl)pyruvate was obtained. The results are shown in the following tables.

(Example 32)

| Starting material: | 2.22 g (10 mmol) |
|---|---|
| Catalyst: | [($\eta^3$-C$_3$H$_5$)Pd(COD)][Tf], |
|  | 40 mg (0.10 mmol) |
| Solvent: | Toluene (10 ml) |
| Reaction temp.: | 110° C. |
| Reaction time: | 2 hrs. |
| Yield: | 100% |

(Example 33)

| Starting material: | 2.22 g (10 mmol) |
|---|---|
| Catalyst: | [Mg][ClO$_4$]$_2$, |
|  | 140 mg (0.63 mmol) |
| Solvent: | Xylene (10 ml) |
| Reaction temp.: | 140° C. |
| Reaction time: | 2 hrs |
| Yield: | 100% |

(Example 34)

| Starting material: | 2.22 g (10 mmol) |
|---|---|
| Catalyst: | [Rh(COD)$_2$][Tf], |
|  | 50 mg (0.10 mmol) |
| Solvent: | Toluene (10 ml) |
| Reaction temp.: | 110° C. |
| Reaction time: | 2 hrs. |
| Yield: | 100% |

EXAMPLE 35

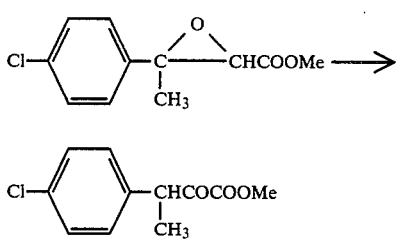

Methyl 3-methyl-3-(4-chlorophenyl)glycidate was isomerized in the same manner as in Example 27, whereby methyl 3-methyl-3-(4-chlorophenyl)pyruvate was obtained. The results are shown in the following table.

(Example 35)

| Starting material: | 2.27 g (10 mmol) |
|---|---|
| Catalyst: | [($\eta^3$-C$_3$H$_5$)Pd(COD)][Tf], |
|  | 40 mg (0.10 mmol) |
| Solvent: | Toluene (10 ml) |
| Reaction temp.: | 110° C. |
| Reaction time: | 5 hrs. |
| Yield: | 100% |

EXAMPLE 36

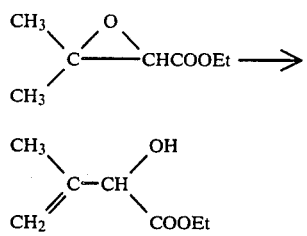

Ethyl 3,3-dimethylglycidate (1.44 g, 10 mmol), allyl(1,5-cyclooctadiene)palladium trifluoromethanesulfonate (40 mg, 0.1 mmol) as a catalyst and benzene (10 ml) as a solvent, were introduced into a 25 ml egg plant type flask, and stirred for 2 hours under reflux. The solvent was removed under reduced pressure, and hexane (about 15ml) and ether (about 5 ml) were added to the residue. The precipitates were filtered. The solvent was completely distilled off from the filtrate, whereby 1.40 g of oily substance was obtained. From the nuclear magnetic resonance spectrum and the infrared absorption spectrum, this substance was found to be substantially pure ethyl 2-hydroxy-3-methyl-3-butenoate. The yield was 98%. The results are shown in the following table.

(Example 36)

| Starting material: | 1.44 g (10 mmol) |
|---|---|
| Catalyst: | [($\eta^3$-C$_3$H$_5$)Pd(COD)][Tf], |
|  | 40 mg (0.10 mmol) |
| Solvent: | Benzene (10 ml) |
| Reaction temp.: | 60° C. |
| Reaction time: | 1 hr. |
| Yield: | 98% |

EXAMPLES 37 AND 38

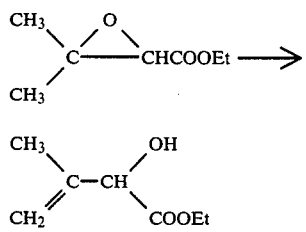

By using ethyl 3,3-dimethylglycidate as a starting material, ethyl 2-hydroxy-3-methyl-3-butenoate was obtained in the same manner as in Example 36. The results are shown in the following tables.

(Example 37)

| Starting material: | 1.44 g (10 mmol) |
|---|---|
| Catalyst: | [($\eta^3$-C$_3$H$_5$)Pd(NBD)][Tf], 3.9 mg (0.01 mmol) |
| Solvent: | Benzene (10 ml) |
| Reaction temp.: | 80° C. |
| Reaction time: | 2 hrs. |
| Yield: | 100% |

(Example 38)

| Starting material: | 2.00 g (14 mmol) |
|---|---|
| Catalyst: | [(MeO—C$_8$H$_{12}$)Pd(COD)][Tf], 5.0 mg (0.01 mmol) |
| Solvent: | Methylene chloride (10 ml) |
| Reaction temp.: | 50° C. |
| Reaction time: | 1 hr. |
| Yield: | 72% |

EXAMPLE 39

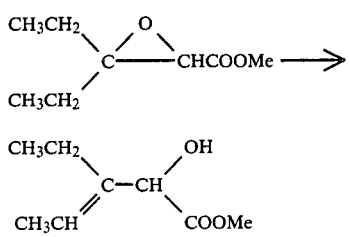

By using methyl 3,3-diethylglycidate as a starting material, methyl 2-hydroxy-3-ethyl-3-pentenoate was obtained by conducting the reaction in the same manner as in Example 36. The results are shown in the following table.

(Example 39)

| Starting material: | 1.58 g (10 mmol) |
|---|---|
| Catalyst: | [($\eta^3$-C$_3$H$_5$)Pd(COD)][Tf], 40 mg (0.10 mmol) |
| Solvent: | Benzene (10 ml) |
| Reaction temp.: | 80° C. |
| Reaction time: | 2 hrs. |
| Yield: | 100% |

EXAMPLES 40 TO 43

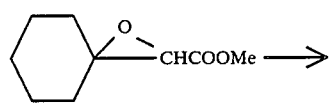

By using methyl 2,3-epoxycyclohexylidene acetate, methyl 2-hydroxy-2-(1-cyclohexenyl)acetate was obtained by conducting the reaction in the same manner as in Example 36. The results are shown in the following tables.

(Example 40)

| Starting material: | 1.69 g (10 mmol) |
|---|---|
| Catalyst: | [($\eta^3$-C$_3$H$_5$)Pd(COD)][Tf], 40 mg (0.10 mmol) |
| Solvent: | Benzene (10 ml) |
| Reaction temp.: | 80° C. |
| Reaction time: | 2 hrs. |
| Yield: | 100% |

(Example 41)

| Starting material: | 5.36 g (32 mmol) |
|---|---|
| Catalyst: | [(MeO—C$_8$H$_{12}$)Pd(COD)][Tf], 27.6 mg (0.055 mmol) |
| Solvent: | Benzene (10 ml) |
| Reaction temp.: | 80° C. |
| Reaction time: | 3 hrs. |
| Yield: | 100% |

(Example 42)

| Starting material: | 1.69 g (10 mmol) |
|---|---|
| Catalyst: | [Rh(COD)$_2$][ClO$_4$], 100 mg (0.25 mmol) |
| Solvent: | Benzene (10 ml) |
| Reaction temp.: | 80° C. |
| Reaction time: | 2 hrs. |
| Yield: | 86% |

(Example 43)

| Starting material: | 2.00 g (12 mmol) |
|---|---|
| Catalyst: | [Ag][Tf], 1.0 mg (0.004 mmol) |
| Solvent: | Benzene (10 ml) |
| Reaction temp.: | 80° C. |
| Reaction time: | 2 hrs. |
| Yield | 98% |

EXAMPLES 44 TO 46

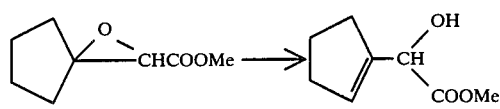

By using methyl 2,3-epoxycyclopentylidene acetate, methyl 2-hydroxy-2-(1-cyclopentenyl)acetate was obtained by conducting the reaction in the same manner as in Example 36. The results are shown in the following tables.

(Example 44)

| Starting material: | 1.56 g (10 mmol) |
|---|---|
| Catalyst: | [($\eta^3$-C$_3$H$_5$)Pd(COD)][Tf], 40 mg (0.10 mmol) |
| Solvent: | Benzene (10 ml) |
| Reaction temp.: | 50° C. |
| Reaction time: | 2.5 hrs. |
| Yield: | 100% |

(Example 45)

| Starting material: | 1.56 g (10 mmol) |
| --- | --- |
| Catalyst: | [($\eta^3$-C$_3$H$_5$)Pd(COD)][ClO$_4$], 36 mg (0.10 mmol) |
| Solvent: | Benzene (10 ml) |
| Reaction temp.: | 80° C. |
| Reaction time: | 2 hrs. |
| Yield: | 100% |

(Example 46)

| Starting material: | 1.56 g (10 mmol) |
| --- | --- |
| Catalyst: | [Zn][ClO$_4$]$_2$, 26 mg (0.1 mmol) |
| Solvent: | Toluene (15 ml) |
| Reaction temp.: | 90° C. |
| Reaction time: | 3 hrs. |
| Yield: | 100% |

EXAMPLE 47

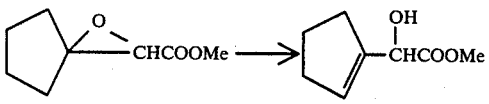

Methyl 2,3-epoxycyclopentylidene acetate was isomerized by using Nafion-Ag (synthesized from Nafion-H manufactured by DuPont Co. and AgNO$_3$) as a catalyst, whereby methyl 2-hydroxy-2-(1-cyclopentenyl)acetate was obtained. The results are shown in the following table.

(Example 47)

| Starting material: | 1.56 g (10 mmol) |
| --- | --- |
| Catalyst: | Nafion—Ag, 10 mg |
| Solvent: | Benzene (10 ml) |
| Reaction temp.: | 80° C. |
| Reaction time: | 2 hrs. |
| Yield: | 100% |

EXAMPLES 48 TO 50

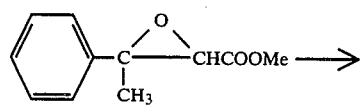

By using ethyl 3-butyl-3-methyl-glycidate as a starting material, the reaction was conducted in the same manner as in Example 36, whereby a mixture comprising ethyl 2-hydroxy-3-methyl-3-heptenoate and ethyl 2-hydroxy-3-butyl-3-butenoate, was obtained. Their production ratios were determined by the nuclear magnetic resonance spectrum. The results are shown in the following tables.

(Example 48)

| Starting material: | 1.86 g (10 mmol) |
| --- | --- |
| Catalyst: | [($\eta^3$-C$_3$H$_5$)Pd(COD)][Tf], 40 mg (0.10 mmol) |
| Solvent: | Benzene (10 ml) |
| Reaction temp.: | 80° C. |
| Reaction time: | 2 hrs. |
| Yield: | 100% |

(Example 49)

| Starting material: | 1.00 g (5.4 mmol) |
| --- | --- |
| Catalyst: | [($\eta^3$-C$_3$H$_5$)Pd(COD)][ClO$_4$], 50 mg (0.14 mmol) |
| Solvent: | Benzene (10 ml) |
| Reaction temp.: | 60° C. |
| Reaction time: | 1 hr. |
| Yield: | 100% |

(Example 50)

| Starting material: | 2.20 g (11.8 mmol) |
| --- | --- |
| Catalyst: | [Rh(COD)$_2$][ClO$_4$], 100 mg (0.25 mmol) |
| Solvent: | Benzene (10 ml) |
| Reaction temp.: | 80° C. |
| Reaction time: | 2 hrs. |
| Yield: | 95% |

| | Ethyl 2-hydroxy-3-methyl-3-heptenoate | Ethyl 2-hydroxy-3-butyl-3-butenoate |
| --- | --- | --- |
| Example 48 | 70% | 30% |
| Example 49 | 61% | 39% |
| Example 50 | 76% | 24% |

(The production ratios were determined by the integral ratios of the nuclear magnetic resonance spectra.)

EXAMPLES 51 TO 57

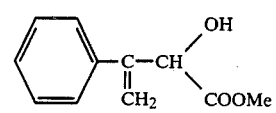

By using methyl 3-methyl-3-phenylglycidate as a starting material, the reaction was conducted in the same manner as in Example 36, whereby methyl 2-hydroxy-3-phenyl-3-butenoate was obtained. The results are shown in the following tables.

(Example 51)

| Starting material: | 19.2 g (100 mmol) |
| --- | --- |
| Catalyst: | [($\eta^3$-C$_3$H$_5$)Pd(COD)][Tf], 403 mg (1 mmol) |
| Solvent: | Benzene (100 ml) |
| Reaction temp.: | 80° C. |
| Reaction time: | 2 hrs. |

-continued

| | |
|---|---|
| Yield: | 100% |

(Example 52)

| | |
|---|---|
| Starting material: | 1.92 g (10 mmol) |
| Catalyst: | [(η³-C₃H₅)Pd(COD)][Tf], 40 mg (0.10 mmol) |
| Solvent: | Benzene (10 ml) |
| Reaction temp.: | 60° C. |
| Reaction time: | 2 hrs. |
| Yield: | 100% |

(Example 53)

| | |
|---|---|
| Starting material: | 1.92 g (10 mmol) |
| Catalyst: | [(η³-C₃H₅)Pd(COD)[ClO₄], 36 mg (0.10 mmol) |
| Solvent: | Benzene (10 ml) |
| Reaction temp.: | 80° C. |
| Reaction time: | 2 hrs. |
| Yield: | 100% |

(Example 54)

| | |
|---|---|
| Starting material: | 1.92 g (10 mmol) |
| Catalyst: | [(MeO—C₈H₁₂)Pd(COD)][Tf], 50 mg (0.10 mmol) |
| Solvent: | Benzene (10 ml) |
| Reaction temp.: | 80° C. |
| Reaction time: | 2 hrs. |
| Yield: | 95% |

(Example 55)

| | |
|---|---|
| Starting material: | 1.92 g (10 mmol) |
| Catalyst: | [Rh(COD)₂][ClO₄], 40 mg (0.10 mmol) |
| Solvent: | Benzene (10 ml) |
| Reaction temp.: | 80° C. |
| Reaction time: | 2 hrs. |
| Yield: | 90% |

(Example 56)

| | |
|---|---|
| Starting material: | 1.92 g (10 mmol) |
| Catalyst: | [Zn][ClO₄]₂, 26 mg (0.10 mmol) |
| Solvent: | Toluene (15 ml) |
| Reaction temp.: | 90° C. |
| Reaction time: | 2 hrs. |
| Yield: | 100% |

(Example 57)

| | |
|---|---|
| Starting material: | 1.92 g (10 mmol) |
| Catalyst: | [Mg][ClO₄]₂, 47 mg (0.20 mmol) |
| Solvent: | Toluene (15 ml) |
| Reaction temp.: | 110° C. |
| Reaction time: | 4 hrs. |
| Yield: | 100% |

EXAMPLES 58 AND 59

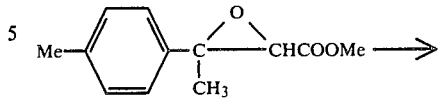

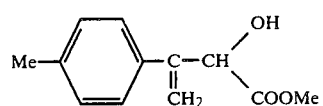

By using methyl 3-methyl-3-(4-methylphenyl)glycidate as a starting material, methyl 2-hydroxy-3-(4-methylphenyl)-3-butenoate was obtained in the same manner as in Example 36. The results are shown in the following tables.

(Example 58)

| | |
|---|---|
| Starting material: | 2.06 g (10 mmol) |
| Catalyst: | [(η³-C₃H₅)Pd(COD)][Tf], 4.0 mg (0.01 mmol) |
| Solvent: | Benzene (5 ml) |
| Reaction temp.: | 80° C. |
| Reaction time: | 3 hrs. |
| Yield: | 100% |

(Example 59)

| | |
|---|---|
| Starting material: | 10.3 g (50 mmol) |
| Catalyst: | [Zn][ClO₄]₂, 132 mg (0.50 mmol) |
| Solvent: | Toluene (100 ml) |
| Reaction temp.: | 80° C. |
| Reaction time: | 2.5 hrs. |
| Yield: | 100% |

EXAMPLES 60 TO 64

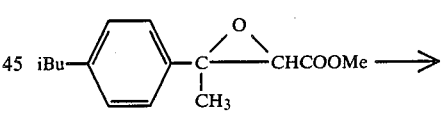

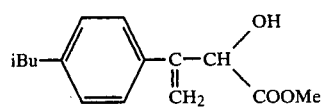

By using methyl 3-methyl-3-(4-isobutylphenyl)glycidate as a starting material, methyl 2-hydroxy-3-(4-isobutylphenyl)-3-butenoate was obtained in the same manner as in Example 36. The results are shown in the following tables.

(Example 60)

| | |
|---|---|
| Starting material: | 2.48 g (10 mmol) |
| Catalyst: | [(η³-C₃H₅)Pd(COD)][Tf], 41 mg (0.10 mmol) |
| Solvent: | Benzene (5 ml) |
| Reaction temp.: | 80° C. |
| Reaction time: | 2 hrs. |
| Yield: | 100% |

(Example 61)

| | |
|---|---|
| Starting material: | 2.48 g (10 mmol) |
| Catalyst: | [($\eta^3$-C$_3$H$_5$)Pd(COD)][Tf], 0.8 mg (0.002 mmol) |
| Solvent: | Benzene (5 ml) |
| Reaction temp.: | 75° C. |
| Reaction time: | 2 hrs. |
| Yield: | 100% |

(Example 62)

| | |
|---|---|
| Starting material: | 2.48 g (10 mmol) |
| Catalyst: | [($\eta^3$-C$_3$H$_5$)Pd(COD)][ClO$_4$], 35 mg (0.10 mmol) |
| Solvent: | Benzene (10 ml) |
| Reaction temp.: | 80° C. |
| Reaction time: | 2 hrs. |
| Yield: | 100% |

(Example 63)

| | |
|---|---|
| Starting material: | 2.48 g (10 mmol) |
| Catalyst: | [Rh(COD$_2$)][ClO$_4$], 40 mg (0.10 mmol) |
| Solvent: | Benzene (10 ml) |
| Reaction temp.: | 80° C. |
| Reaction time: | 2 hrs. |
| Yield: | 100% |

(Example 64)

| | |
|---|---|
| Starting material: | 2.48 g (10 mmol) |
| Catalyst: | [Zn][ClO$_4$]$_2$, 26 mg (0.10 mmol) |
| Solvent: | Toluene (10 ml) |
| Reaction temp.: | 80° C. |
| Reaction time: | 2 hrs. |
| Yield: | 100% |

EXAMPLES 65 TO 68

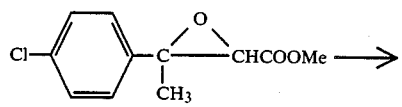

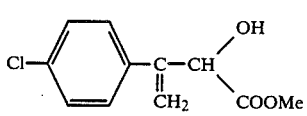

By using methyl 3-methyl-3-(4-chlorophenyl)glycidate as a starting material, methyl 2-hydroxy-3-(4-chlorophenyl)-3-butenoate was obtained in the same manner as in Example 36. The results are shown in the following tables.

(Example 65)

| | |
|---|---|
| Starting material: | 22.7 g (100 mmol) |
| Catalyst: | [($\eta^3$-C$_3$H$_5$)Pd(COD)][Tf], 40 mg (0.10 mmol) |
| Solvent: | Benzene (100 ml) |
| Reaction temp.: | 80° C. |
| Reaction time: | 2 hrs. |
| Yield: | 95% |

(Example 66)

| | |
|---|---|
| Starting material: | 2.00 g (8.8 mmol) |
| Catalyst: | [Ag][Tf], 10 mg (0.04 mmol) |
| Solvent: | Benzene (10 ml) |
| Reaction temp.: | 80° C. |
| Reaction time: | 2 hrs. |
| Yield: | 90% |

(Example 67)

| | |
|---|---|
| Starting material: | 1.02 g (4.5 mmol) |
| Catalyst: | [Zn][ClO$_4$]$_2$, 3.0 mg (0.01 mmol) |
| Solvent: | Benzene (10 ml) |
| Reaction temp.: | 80° C. |
| Reaction time: | 2 hrs. |
| Yield: | 97% |

(Example 68)

| | |
|---|---|
| Starting material: | 1.05 g (4.6 mmol) |
| Catalyst: | [Mg][ClO$_4$]$_2$, 30 mg (0.13 mmol) |
| Solvent: | Benzene (10 ml) |
| Reaction temp.: | 80° C. |
| Reaction time: | 3 hrs. |
| Yield: | 100% |

EXAMPLE 69

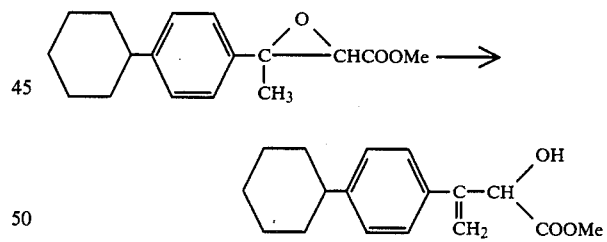

By using methyl 3-methyl-3-(4-cyclohexylphenyl)-glycidate, the isomerization reaction was conducted in the same manner as in Example 36, whereby methyl 2-hydroxy-3-(4-cyclohexylphenyl)-3-butenoate was obtained. The results are shown in the following table.

(Example 69)

| | |
|---|---|
| Starting material: | 13.7 g (50 mmol) |
| Catalyst: | [($\eta^3$-C$_3$H$_5$)Pd(COD)][Tf], 40 mg (0.10 mmol) |
| Solvent: | Benzene (100 ml) |
| Reaction temp.: | 80° C. |
| Reaction time: | 2 hrs. |
| Yield: | 100% |

EXAMPLE 70

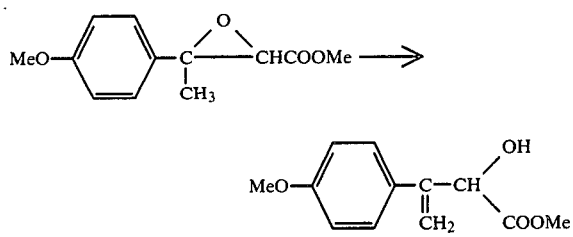

By using methyl 3-methyl-3-(4-methoxyphenyl)glycidate, the reaction was conducted in the same manner as in Example 36, whereby methyl 2-hydroxy-3-(4-methoxyphenyl)-3-butenoate was obtained. The results are shown in the following table.

(Example 70)

| Starting material: | 2.22 g (10 mmol) |
|---|---|
| Catalyst: | [(η³-C₃H₅)Pd(COD)][Tf], 40 mg (0.01 mmol) |
| Solvent: | Benzene (10 ml) |
| Reaction temp.: | 80° C. |
| Reaction time: | 2 hrs. |
| Yield: | 100% |

EXAMPLES 71 and 72

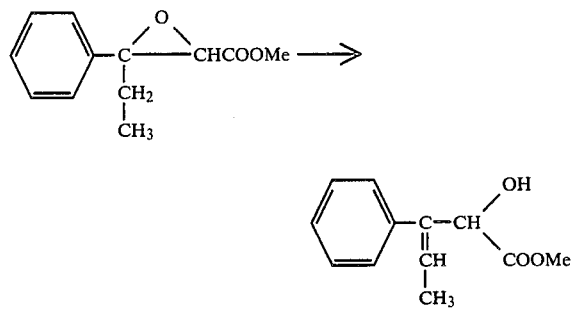

By using methyl 3-ethyl-3-phenylglycidate as a starting material, the reaction was conducted in the same manner as in Example 36, whereby methyl 2-hydroxy-3-phenyl-3-pentenoate was obtained. The results are shown in the following tables.

(Example 71)

| Starting material: | 2.06 g (10 mmol) |
|---|---|
| Catalyst: | [(η³-C₃H₅)Pd(COD)][Tf], 40 mg (0.10 mmol) |
| Solvent: | Benzene (10 ml) |
| Reaction temp.: | 80° C. |
| Reaction time: | 2 hrs. |
| Yield: | 100% |

(Example 72)

| Starting material: | 2.06 g (10 mmol) |
|---|---|
| Catalyst: | [Zn][ClO₄]₂, 26 mg (0.10 mmol) |
| Solvent: | Toluene (15 ml) |
| Reaction temp.: | 90° C. |
| Reaction time: | 3 hrs. |
| Yield: | 100% |

EXAMPLE 73

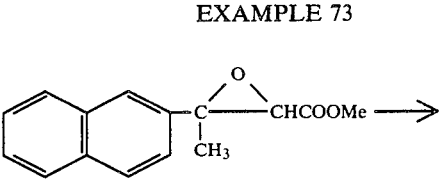

By using methyl 3-methyl-3-(2-naphthyl)glycidate as a starting material, methyl 2-hydroxy-3-(2-naphthyl)-3-butenoate was obtained in the same manner as in Example 36. The results are shown in the following table.

(Example 73)

| Starting material: | 2.42 g (10 mmol) |
|---|---|
| Catalyst: | [(η³-C₃H₅)Pd(COD)][Tf], 40 mg (0.10 mmol) |
| Solvent: | Benzene (10 ml) |
| Reaction temp.: | 80° C. |
| Reaction time: | 2 hrs. |
| Yield: | 95% |

EXAMPLES 74 and 75

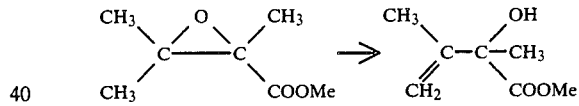

By using methyl 2,3,3-trimethylglycidate as a starting material, methyl 2-hydroxy-2,3-dimethyl-3-butenoate was obtained by the reaction in the same manner as in Example 36. The results are shown in the following tables.

(Example 74)

| Starting material: | 1.44 g (10 mmol) |
|---|---|
| Catalyst: | [(η³-C₃H₅)Pd(COD)][Tf], 40 mg (0.10 mmol) |
| Solvent: | Benzene (10 ml) |
| Reaction temp.: | 80° C. |
| Reaction time: | 2 hrs. |
| Yield: | 100% |

(Example 75)

| Starting material: | 1.44 g (10 mmol) |
|---|---|
| Catalyst: | [(η³-C₃H₅)Pd(COD)][ClO₄], 36 mg (0.10 mmol) |
| Solvent: | Benzene (10 ml) |
| Reaction temp.: | 80° C. |
| Reaction time: | 2 hrs. |
| Yield: | 100% |

EXAMPLES 76 and 77

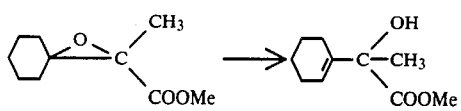

By using methyl 2-methyl-2,3-epoxycyclohexylidene acetate as a starting material, methyl 2-hydroxy-2-(1-cyclohexenyl)propionate was obtained in the same manner as in Example 36. The results are shown in the following tables.

(Example 76)

| Starting material: | 36.3 g (197 mmol) |
|---|---|
| Catalyst: | $[(\eta^3\text{-}C_3H_5)Pd(COD)][Tf]$, 100 mg (0.25 mmol) |
| Solvent: | Benzene (20 ml) |
| Reaction temp.: | 80° C. |
| Reaction time: | 2 hrs. |
| Yield: | 100% |

(Example 77)

| Starting material: | 4.0 g (22 mmol) |
|---|---|
| Catalyst: | $[Rh(COD)_2][Tf]$, 20 mg (0.05 mmol) |
| Solvent: | Benzene (20 ml) |
| Reaction temp.: | 80° C. |
| Reaction time: | 2 hrs. |
| Yield: | 96% |

EXAMPLE 78

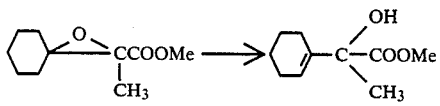

Methyl 2-methyl-2,3-epoxycyclohexylidene acetate was isomerized by using Nafion-Ag (synthesized from Nafion-H manufactured by DuPont Co. and AgNO₃) as a catalyst, whereby methyl 2-hydroxy-2-(1-cyclohexenyl)propionate was obtained. The results are shown in the following table.

(Example 78)

| Starting material: | 2.00 g (10 mmol) |
|---|---|
| Catalyst: | Nafion—Ag, 10 mg |
| Solvent: | Benzene (10 ml) |
| Reaction temp.: | 80° C. |
| Reaction time: | 2 hrs. |
| Yield: | 100% |

EXAMPLES 79 to 81

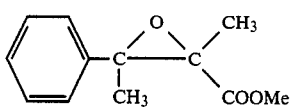

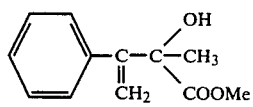

By using methyl 2,3-dimethyl-3-phenylglycidate as a starting material, methyl 2-hydroxy-2-methyl-3-phenyl-3-butenoate was obtained by the reaction conducted in the same manner as in Example 36. The results are shown in the following tables.

(Example 79)

| Starting material: | 2.06 g (10 mmol) |
|---|---|
| Catalyst: | $[(\eta^3\text{-}C_3H_5)Pd(COD)][Tf]$, 40 mg (0.10 mmol) |
| Solvent: | Benzene (10 ml) |
| Reaction temp.: | 80° C. |
| Reaction time: | 2 hrs. |
| Yield: | 100% |

(Example 80)

| Starting material: | 2.06 g (10 mmol) |
|---|---|
| Catalyst: | $[(\eta^3\text{-}C_3H_5)Pd(COD)][ClO_4]$, 36 mg (0.10 mmol) |
| Solvent: | Benzene (10 ml) |
| Reaction temp.: | 80° C. |
| Reaction time: | 2 hrs. |
| Yield: | 100% |

(Example 81)

| Starting material: | 2.06 g (10 mmol) |
|---|---|
| Catalyst: | $[Rh(COD)_2][Tf]$, 40 mg (0.10 mmol) |
| Solvent: | Benzene (10 ml) |
| Reaction temp.: | 80° C. |
| Reaction time: | 2 hrs. |
| Yield: | 92% |

EXAMPLES 82 and 83

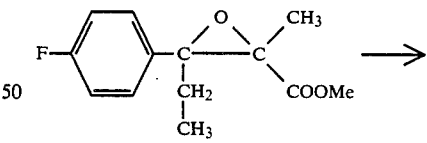

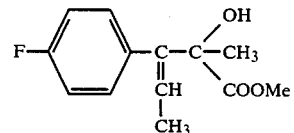

By using methyl 2-methyl-3-ethyl-3-(4-fluorophenyl)-glycidate as a starting material, methyl 2-hydroxy-2-methyl-3-(4-fluorophenyl)-3-pentenoate was obtained in the same manner as in Example 36. The results are shown in the following tables.

(Example 82)

| Starting material: | 2.38 g (10 mmol) |
|---|---|

| | |
|---|---|
| Catalyst: | [(η³-C₃H₅)Pd(COD)][Tf], 140 mg (0.45 mmol) |
| Solvent: | Toluene (10 ml) |
| Reaction temp.: | 100° C. |
| Reaction time: | 6 hrs. |
| Yield: | 80% |

(Example 83)

| | |
|---|---|
| Starting material: | 2.38 g (10 mmol) |
| Catalyst: | [Zn][ClO₄]₂, 60 mg (0.23 mmol) |
| Solvent: | Xylene (10 ml) |
| Reaction temp.: | 140° C. |
| Reaction time: | 2 hrs. |
| Yield: | 86% |

EXAMPLE 84

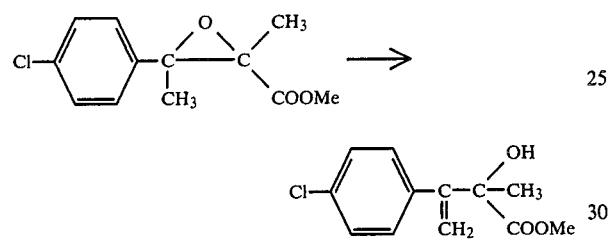

By using methyl 2-methyl-3-ethyl-3-(4-chlorophenyl)glycidate as a starting material, methyl 2-hydroxy-2-methyl-3-(4-chlorophenyl)-3-butenoate was obtained in the same manner as in Example 36. The results are shown in the following table.

(Example 84)

| | |
|---|---|
| Starting material: | 4.88 g (20.3 mmol) |
| Catalyst: | [Zn][ClO₄]₂, 10 mg (0.027 mmol) |
| Solvent: | Benzene (40 ml) |
| Reaction temp.: | 80° C. |
| Reaction time: | 5 hrs. |
| Yield: | 100% |

EXAMPLE 85

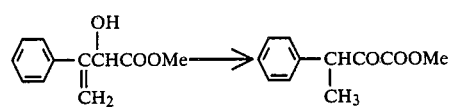

Methyl 2-hydroxy-3-phenyl-3-butenoate (1.92 g, 10 mmol), allyl(1,5-cyclooctadiene)palladium trifluoromethanesulfonate (40 mg, 0.10 mmol) as a catalyst and toluene (10 ml) as a solvent, were introduced into a 25 ml egg plant type flask, and stirred for 3 hours under reflux. After cooling the reaction mixture, the solvent was distilled off under reduced pressure. Hexane and ether were added to the residue, and the precipitates were filtered off. The solvent was completely distilled off from the filtrate, whereby 1.90 g of oily substance was obtained. From the nuclear magnetic resonance spectrum and the infrared absorption spectrum, this substance was found to be pure methyl 3-methyl-3-phenylpyruvate. The results are shown in the following table.

(Example 85)

| | |
|---|---|
| Starting material: | 1.92 g (10 mmol) |
| Catalyst: | [(η³-C₃H₅)Pd(COD)][Tf], 40 mg (0.10 mmol) |
| Solvent: | Toluene (10 ml) |
| Reaction temp.: | 110° C. |
| Reaction time: | 3 hrs. |
| Yield: | 100% |

EXAMPLE 86

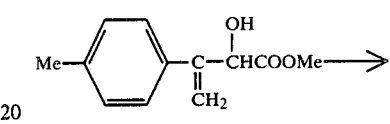

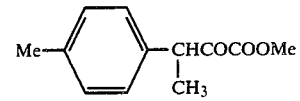

By using allyl(1,5-cyclooctadiene)palladium trifluoromethanesulfonate as a catalyst, methyl 2-hydroxy-3-(4-methylphenyl)-3-butenoate was isomerized by the reaction in the same manner as in Example 85, whereby methyl 3-methyl-3-(4-methylphenyl)pyruvate was obtained. The results are shown in the following table.

(Example 86)

| | |
|---|---|
| Starting material: | 2.06 g (10 mmol) |
| Catalyst: | [(η³-C₃H₅)Pd(COD)][Tf], 40 mg (0.10 mmol) |
| Solvent: | Toluene (10 ml) |
| Reaction temp.: | 110° C. |
| Reaction time: | 3 hrs. |
| Yield: | 96% |

EXAMPLE 87

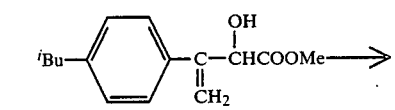

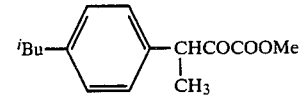

By using allyl(1,5-cyclooctadiene)palladium trifluoromethanesulfonate as a catalyst, methyl 2-hydroxy-3-(4-isobutylphenyl)-3-butenoate was reacted in the same manner as in Example 85, whereby methyl 3-methyl-3-(4-isobutylphenyl)pyruvate was obtained. The results are shown in the following table.

(Example 87)

| | |
|---|---|
| Starting material: | 2.48 g (10 mmol) |
| Catalyst: | [(η³-C₃H₅)Pd(COD)][Tf], 41 mg (0.10 mmol) |
| Solvent: | Toluene (15 ml) |

EXAMPLE 88

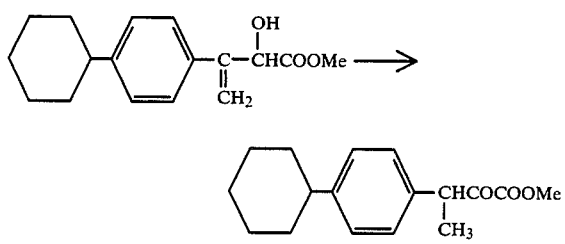

By using allyl(1,5-cyclooctadiene)palladium trifluoromethanesulfonate as a catalyst, methyl 2-hydroxy-3-(4-cyclohexylphenyl)-3-butenoate was reacted in the same manner as in Example 85, whereby methyl 3-methyl-3-(4-cyclohexylphenyl)pyruvate was obtained. The results are shown in the following table.

(Example 88)

| | |
|---|---|
| Starting material: | 2.00 g (7.3 mmol) |
| Catalyst: | [(η³-C₃H₅)Pd(COD)][Tf], 40 mg (0.10 mmol) |
| Solvent: | Toluene (15 ml) |
| Reaction temp.: | 110° C. |
| Reaction time: | 3 hrs. |
| Yield: | 85% |

EXAMPLE 89

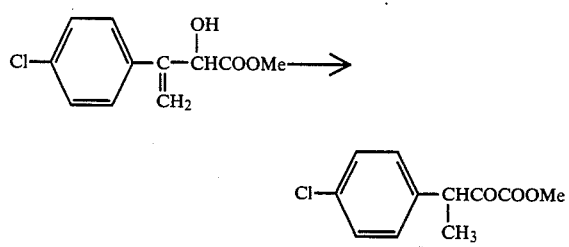

By using allyl(1,5-cyclooctadiene)palladium trifluoromethanesulfonate as a solvent, methyl 2-hydroxy-3-(4-chlorophenyl)-3-butenoate was reacted in the same manner as in Example 85, whereby methyl 3-methyl-3-(4-chlorophenyl)pyruvate was obtained. The results are shown in the following table.

(Example 89)

| | |
|---|---|
| Starting material: | 2.27 g (10 mmol) |
| Catalyst: | [(η³-C₃H₅)Pd(COD)][Tf], 40 mg (0.10 mmol) |
| Solvent: | Toluene (10 ml) |
| Reaction temp.: | 110° C. |
| Reaction time: | 10 hrs. |
| Yield: | 90% |

EXAMPLE 90

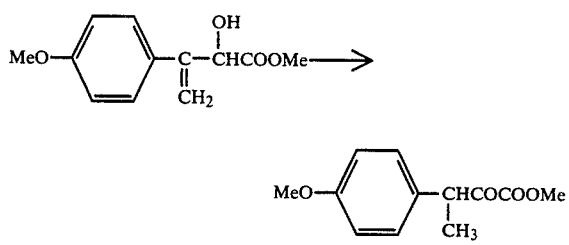

By using allyl(1,5-cyclooctadiene)palladium trifluoromethanesulfonate as a catalyst, methyl 2-hydroxy-3-(4-methoxyphenyl)-3-butenoate was reacted in the same manner as in Example 85, whereby methyl 3-methyl-3-(4-methoxyphenyl)pyruvate was obtained. The results are shown in the following table.

(Example 90)

| | |
|---|---|
| Starting material: | 2.22 g (10 mmol) |
| Catalyst: | [(η³-C₃H₅)Pd(COD)][Tf], 40 mg (0.10 mmol) |
| Solvent: | Toluene (10 ml) |
| Reaction temp.: | 110° C. |
| Reaction time: | 5 hrs. |
| Yield: | 100% |

-continued

| | |
|---|---|
| Reaction temp.: | 110° C. |
| Reaction time: | 3 hrs. |
| Yield: | 100% |

The nuclear magnetic resonance spectrum data and infrared absorption spectrum data of the arylpyruvates and 2-hydroxycarboxylates obtained by the reactions in Examples 1 to 90, are listed in the following table.

| Example | | NMR spectrum (CDCl₃, TMS, δppm) | IR spectrum cm⁻¹ $\nu$OH | $\nu$CO |
|---|---|---|---|---|
| | Arylpyruvate | | | |
| 1–3 | Methyl 3-phenylpyruvate | 3.20 (brs, 1H), 3.87 (s, 3H), 6.52 (s, 1H), 7.0~7.8 (m, 5H). | 3450 | 1746 1705 |
| 4, 5 | Ethyl 3-phenylpyruvate | 1.36 (1, 3H), 4.33 (q, 2H), 6.5 (s, 1H), 7.0~8.0 (m, 5H). | 3460 | 1733 1695 |
| 6–8 | Methyl 3-(4-methylphenyl)pyruvate | 2.33 (s, 3H), 3.85 (s, 3H), 6.26 (brs, 1H), 6.46 (s, 1H). 7.11 (d, 2H), 7.61 (d, 2H). | 3470 | 1750 1705 |
| 9, 10 | Methyl 3-(4-ethylphenyl)-pyruvate | 1.20 (t, 3H), 2.60 (q, 2H), 3.86 (s, 3H), 6.43 (s, 1H), 6.50 (s, 1H), 7.16 (d, 2H), 7.69 (d, 2H). | 3460 | 1745 1700 |
| 11, 12 | Methyl 3-(4-isopropylphenyl)pyruvate | 1.0~1.4 (m, 3H), 2.83 (sep, 1H), 3.81 (s, 3H), 6.38 (s, 1H) 6.47 (s, 1H), 7.0~7.9 (m, 4H). | 3470 | 1740 1695 |
| 13–16 122 | Methyl 3-(4-fluorophenyl)pyruvate | 3.81 (s, 3H), 3.86 (s, 3H), 6.50 (s, 1H), 6.56 (brs, 1H), 6.8~7.9 (m, 4H). | 3430 | 1735 1700 |

-continued

| Example | | NMR spectrum (CDCl₃, TMS, δppm) | IR spectrum cm⁻¹ νOH | νCO |
|---|---|---|---|---|
| 17, 18 123 | Methyl 3-(4-chlorophenyl) pyruvate | 3.88 (s, 3H), 6.45 (brs, 1H), 7.28 (d, 2H) 7.68 (d, 2H). | 3420 | 1740 1700 |
| 19, 20 | Ethyl 3-(4-chlorophenyl)- pyruvate | 1.35 (t, 3H), 4.38 (q, 2H), 5.80 (m, 1H), 6.43 (s, 1H), 7.37 (d, 2H), 7.77 (d, 2H). | 3440 | 1733 1695 |
| 21–23 | Methyl 3-(4-methoxy- phenyl)pyruvate | 3.77 (s, 3H), 3.82 (s, 3H) 6.35 (brs, 1H), 6.48 (s, 1H) 6.6~7.9 (m, 4H). | 3460 | 1750 1700 |
| 24 | Methyl 3-(3-methoxy- phenyl)pyruvate | 3.77 (s, 3H), 3.81 (s, 3H), 6.43 (brs, 1H), 6.5~7.5 (m, 4H). | 3450 | 1745 1695 |
| 25 | Ethyl 3-(3,4-dimethoxy- phenyl)pyruvate | 1.37 (t, 3H), 3.87 (s, 6H), 4.67 (q, 2H), 6.45 (s, 1H), 6.73 (brs, 1H), 7.16~7.57 (m, 3H). | 3430 | 1735 1695 |
| 26 | Methyl 3-(2-naphthyl)- pyruvate | 3.85 (s, 3H), 6.63 (brs, 1H), 6.65 (brs, 1H), 7.3~8.0 (m, 7H). | 3420 | 1739 1706 |
| 27, 28, 87 125–127 | Methyl 3-methyl-3-(4- isobutylphenyl)pyruvate | 0.88 (d, 6H), 1.43 (d, 3H), 1.80 (m, 1H), 2.45 (d, 2H), 3.67 (s, 3H), 4.47 (q, 1H) 7.08 (m, 4H). | — | 1750 1727 |
| 29, 86 | Methyl 3-methyl-3-(4- methylphenyl)pyruvate | 1.40 (d, 3H), 2.35 (s, 3H), 3.63 (s, 3H), 4.37 (q, 1H) 7.05 (s, 4H). | — | 1750 1730 |
| 30, 31, 85 | Methyl 3-methyl-3-phenyl- pyruvate | 1.33 (d, 3H), 3.53 (s, 3H), 4.43 (q, 1H), 7.13 (s, 5H). | — | 1750 1730 |
| 32–34 90 | Methyl 3-methyl-3-(4- methoxyphenyl)pyruvate | 1.42 (d, 3H), 3.67 (s, 3H), 3.73 (s, 3H), 4.38 (q, 1H), 6.73 (d, 2H), 7.03 (d, 2H). | — | 1748 1729 |
| 35, 89 | Methyl 3-methyl-3-(4- chlorophenyl)pyruvate | 1.43 (d, 3H), 3.70 (s, 3H), 4.43 (q, 1H), 7.12 (m, 4H). | — | 1750 1728 |
| 88 | Methyl 3-methyl-3-(4- cyclohexylphenyl)- pyruvate | 1.40 (d, 3H), 1.07~2.03 (m, 10H), 2.40 (m, 1H), 3.63 (s, 3H), 4.37 (q, 1H), 7.00 (s, 4H). | — | 1752 1734 |
| 124 | Methyl 3-(4-bromo- phenyl)pyruvate | 3.89 (s, 3H), 6.42 and 6.50 (each m, total 2H), 7.30 (m, 4H). | 3425 | 1745 1700 |
| | 2-Hydroxycarboxylate | | | |
| 36–38 | Ethyl 2-hydroxy-3-methyl- 3-butenoate | 1.27 (t, 3H), 1.73 (d, 3H), 3.63 (brs, 1H), 4.20 (q, 2H), 4.47 (s, 1H), 4.97 (q, 1H), 5.10 (brs, 1H). | 3480 | 1735 |
| 39 | Methyl 2-hydroxy-3-ethyl- 3-pentenoate | 0.98 (t, 3H), 1.80 (m, 3H), 2.06 (m, 2H), 3.30 (brs, 1H), 3.73 (s, 3H), 4.51 and 5.07 (each s, total 1H), 5.53 (m, 1H). | 3500 | 1735 |
| 40–43 | Methyl 2-hydroxy-2- (1-cyclohexenyl)acetate | 1.80 (m, 4H), 2.03 (m, 2.97 (s, 1H), 3.77 (s, 3H), 4.43 (s, 1H), 5.77 (m, 1H). | 3500 | 1738 |
| 44–47 | Methyl 2-hydroxy-2- (1-cyclopentenyl)acetate | 1.7~2.7 (m, 6H), 3.30 (brs, 1H), 3.80 (s, 3H), 4.80 (s, 1H), 5.80 (m, 1H). | 3480 | 1735 |
| 48–50 | Ethyl 2-hydroxy-3- methyl-3-heptenoate | 0.90 (t, 3H, J = 7 Hz), 1.27 (t, 3H, J = 7 Hz), 1.30 (m, 2H), 1.60 (br s, 3H), 2.03 (q, 2H, J = 6 Hz), 3.27 (s, 1H), 4.23 (q, 2H, J = 7 Hz), 4.47 (s, 1H), 5.53 (t, 1H). | 3500 | 1737 |
| | Ethyl 2-hydroxy-3- butyl-3-butenoate | 0.90 (t, 3H, J = 7 Hz), 1.27 (t, 3H, J = 7 Hz), 1.2~1.5 (m, 4H), 2.03 (q, 2H, J = 6 Hz), 3.27 (s, 1H), 4.23 (q, 2H, J = 7 Hz), 4.53 (s, 1H), 5.00 (m, 1H), 5.13 (brs, 1H). | | |
| 51–57 | Methyl 2-hydroxy-3- phenyl-3-butenoate | 3.50 (s, 3H), 4.00 (brs, 1H), 5.03 (s, 1H), 5.40 (m, 2H), 7.20 (m, 5H). | 3490 | 1738 |
| 58, 59 | Methyl 2-hydroxy-3- (4-methylphenyl)-3- butenoate | 2.33 (s, 3H), 3.33 (d, 1H, J = 6 Hz), 3.67 (s, 3H), 5.02 (d, 1H, J = 6 Hz), 5.35 (s, 1H), 5.43 (s, 1H), 7.17 (m, 4H). | 3490 | 1737 |
| 60–64 | Methyl 2-hydroxy-3- (4-isobutylphenyl)-3- butenoate | 0.87 (d, 6H, J = 7 Hz), 1.80 (m, 1H), 2.40 (d, 2H, J = 6 Hz), 3.20 (brs, 1H), 3.60 (s, 3H), 4.93 (s, 1H), 5.28 (s, 1H), 5.37 (s, 1H), 7.10~7.50 (m, 4H). | 3500 | 1737 |
| 65–68 | Methyl 2-hydroxy-3- (4-chlorophenyl)-3- butenoate | 3.20 (brs, 1H), 3.70 (s, 3H), 5.00 (s, 1H), 5.43 (s, 1H), 5.47 (s, 1H), 7.30 (m, 1H). | 3500 | 1740 |
| 69 | Methyl 2-hydroxy-3- (4-cyclohexylphenyl)-3- butenoate | 1.1~2.0 (m, 10H), 2.47 (m, 1H), 3.37 (brs, 1H), 3.67 (s, 3H), 5.00 (brs, 1H), 5.30 (s, 1H), 5.43 (s, 1H), 7.10 (d, 2H, J = 9 Hz), 7.30 (d, 2H, J = 9 Hz). | 3490 | 1737 |
| 70 | Methyl 2-hydroxy-3- | 3.25 (d, 1H, J = 6 Hz), 3.70 (s, 3H), | 3490 | 1740 |

-continued

| Example | | NMR spectrum (CDCl₃, TMS, δppm) | IR spectrum cm⁻¹ $\nu$OH | $\nu$CO |
|---|---|---|---|---|
| | (4-methoxyphenyl)-3-butenoate | 3.78 (s, 3H), 5.00 (d, 1H, J = 6 Hz), 5.30 (s, 1H), 5.40 (s, 1H), 6.82 (d, 2H, J = 9 Hz), 7.32 (d, 2H, J = 9 Hz). | | |
| 71, 72 | Methyl 2-hydroxy-3-phenyl-3-pentenoate | 1.60 and 1.87 (each d, total 3H, J = 7 Hz), 2.97 (brs, 1H), 3.63 (s, 3H), 4.73 and 5.22 (each s, total 1H), 5.83 (q, 1H, J = 7 Hz), 7.13 (m, 5H). | 3480 | 1735 |
| 73 | Methyl 2-hydroxy-3-(2-naphthyl)-3-butenoate | 3.50 (brs, 1H), 3.63 (s, 3H), 5.10 (s, 1H), 5.47 (s, 1H), 5.53 (s, 1H), 7.2~7.9 (m, 7H). | 3500 | 1740 |
| 74, 75 | Methyl 2-hydroxy-2,3-dimethyl-3-butenoate | 1.53 (s, 3H), 1.77 (m, 3H), 3.32 (brs, 1H), 3.73 (s, 3H), 4.90 (q, 1H, J = 1Hz), 5.07 (m, 1H). | 3500 | 1734 |
| 76-78 | Methyl 2-hydroxy-2-(1-cyclohexenyl)phopionate | 1.53 (s, 3H), 1.57 (m, 4H), 1.97 (m, 4H), 3.33 (s, 1H), 3.70 (s, 3H), 5.70 (m, 1H). | 3500 | 1735 |
| 79-81 | Methyl 2-hydroxy-2-methyl-3-phenyl-3-butenoate | 1.62 (s, 3H), 3.47 (s, 1H), 3.63 (s, 3H), 3.48 (s, 1H), 5.40 (s, 1H), 7.15 (s, 5H). | 3510 | 1737 |
| 82, 83 | Methyl 2-hydroxy-2-methyl-3-(4-fluorophenyl)-3-pentenoate | 1.43 (d, 3H), 1.53 (s, 3H), 3.38 (brs, 1H), 3.67 (s, 3H), 6.00 (q, 1H), 6.90~7.10 (m, 4H). | 3510 | 1736 |
| 84 | Methyl 2-hydroxy-2-methyl-3-(4-chlorophenyl)-3-butenoate | 1.62 (s, 3H), 3.66 (s, 3H), 4.00 (brs, 1H), 5.31 (d, 2H), 7.10 (s, 4H). | 3530 | 1737 |

REFERENCE EXAMPLE

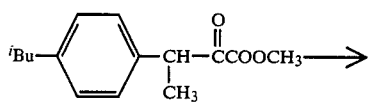

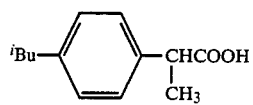

Methyl 3-methyl-3-(4-isobutylphenyl)pyruvate (1.19 g, 4.8 mmol) was dissolved in a 1N sodium hydroxide aqueous solution (15 ml), and a 35% hydrogen peroxide aqueous solution (5.0 ml) was dropwise added under cooling (0° C.) and stirring. The temperature of the mixture was returned to room temperature, and the mixture was stirred overnight. Then, mixture was acidified with hydrochloric acid and extracted with ether, whereby 2-(4-isobutylphenyl)propionic acid (0.78 g, yield: 79%) was obtained.

Nuclear magnetic resonance spectrum (CDCl₃, TMS): δ0.88 (d, 6H), 1.46 (d, 3H), 1.83 (d of sep, 1H), 2.42 (d, 2H), 3.65 (q, 1H), 7.08 (m, 4H)

Infrared absorption spectrum (neat): $\nu$COOH: 1715 cm⁻¹

EXAMPLE 91

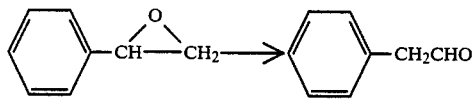

To a benzene (25 ml) solution of styrene oxide (1.20 g, 10 mmol), allyl(1,5-cyclooctadiene)palladium trifluoromethanesulfonate (40 mg, 0.099 mmol) was added, and the mixture was stirred at 50° C. for 30 minutes. After cooling, the obtained reaction solution was analyzed by an internal standard method by means of gas chromatography and the nuclear magnetic resonance spectrum, whereby it was found that the conversion of styrene oxide was 100% and the yield of phenylacetaldehyde was 75%.

EXAMPLES 92 TO 94

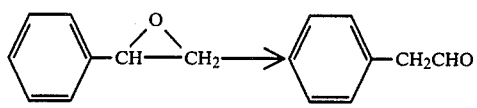

In the same manner as in Example 91, the isomerization reaction of styrene oxide was conducted. The catalyst, the solvent and the reaction conditions are shown in the following tables together with the results.

(Example 92)

| Starting material: | 1.20 g (10 mmol) |
|---|---|
| Catalyst: | [(η³-C₃H₅)Pd(COD)][Tf], 40 mg (0.099 mmol) |
| Solvent: | 1,4-dioxane (25 ml) |
| Reaction temp.: | 50° C. |
| Reaction time: | 20 min. |
| Conversion: | 100% |
| Yield: | 50% |

(Example 93)

| Starting material: | 1.22 g (10 mmol) |
|---|---|
| Catalyst: | [(η³-C₃H₅)Pd{(PhO)₃P}₂]—[ClO₄], 86 mg (0.099 mmol) |
| Solvent: | Benzene (25 ml) |
| Reaction temp.: | 50° C. |
| Reaction time: | 5 min. |
| Conversion: | 100% |
| Yield: | 68% |

(Example 94)

| Starting material: | 1.20 g (10 mmol) |
|---|---|
| Catalyst: | [($\eta^3$-C$_3$H$_5$)Pd{(PhO)$_3$P}$_2$]—[ClO$_4$], 86 mg (0.099 mmol) |
| Solvent: | Benzene (50 ml) |
| Reaction temp.: | 50° C. |
| Reaction time: | 10 min. |
| Conversion: | 100% |
| Yield: | 61% |

EXAMPLES 95 AND 96

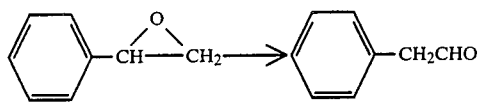

The isomerization reaction of styrene oxide was conducted in the same manner as in Example 91 except that triphenylphosphite was added as a ligand. The catalyst, the solvent and the reaction conditions are shown in the following table together with the results.

(Example 95)

| Starting material: | 1.20 g (10 mmol) |
|---|---|
| Catalyst: | [($\eta^3$-C$_3$H$_5$)Pd(COD)][Tf], 40 mg (0.099 mmol); (PhO$_3$)P, 32 mg (0.10 mmol) |
| Solvent: | Benzene (25 ml) |
| Reaction temp.: | 50° C. |
| Reaction time: | 10 min. |
| Conversion: | 100% |
| Yield: | 59% |

(Example 96)

| Starting material: | 1.20 g (10 mmol) |
|---|---|
| Catalyst: | [($\eta^3$-C$_3$H$_5$)Pd(COD)][Tf], 40 mg (0.099 mmol); (PhO)$_3$P, 32 mg (0.10 mmol) |
| Solvent: | Benzene (40 ml) |
| Reaction temp.: | 50° C. |
| Reaction time: | 10 min. |
| Conversion: | 100% |
| Yield: | 67% |

EXAMPLE 97

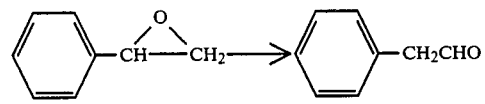

A benzene (20 ml) solution of allyl(1,5-cyclooctadiene)palladium trifluoromethanesulfonate (40 mg, 0.099 mmol) as a catalyst, was heated to 50° C., and a benzene (5 ml) solution of styrene oxide (1.20 g, 10 mmol) was dropwise added thereto over a period of 20 minutes. Then, the mixture was further stirred at 50° C. for 25 minutes. After cooling, the obtained reaction mixture was analyzed by an internal standard method by means of gas chromatography and the nuclear magnetic resonance spectrum, whereby it was found that the conversion of styrene oxide was 100% and the yield of phenylacetaldehyde was 67%.

EXAMPLE 98

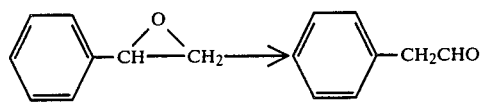

To a benzene (25 ml) solution of styrene oxide (602 mg, 5.0 mmol), bis(1,5-cyclooctadiene)rhodium trifluoromethansulfonate (22 mg, 0.047 mmol) was added as a catalyst, and the mixture was stirred at 40° C. for 10 minutes. After cooling, the obtained reaction mixture was analyzed by an internal standard method by means of gas chromatography and the nuclear magnetic resonance spectrum, whereby it was found that the conversion of styrene oxide was 100% and the yield of phenylacetaldehyde was 70%.

EXAMPLES 99 AND 100

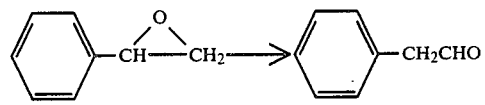

By using a rhodium-type catalyst, the isomerization reaction of styrene oxide was conducted in the same manner as in Example 91. The catalyst, the solvent and the reaction conditions are shown in the following tables together with the results.

(Example 99)

| Starting material: | 633 mg (5.27 mmol) |
|---|---|
| Catalyst: | [Rh(COD){(PhO)$_2$P}$_2$][Tf], 23 mg (0.023 mmol) |
| Solvent: | Benzene (25 ml) |
| Reaction temp.: | 40° C. |
| Reaction time: | 10 min. |
| Conversion: | 100% |
| Yield: | 43% |

(Example 100)

| Starting material: | 713 g (5.93 mmol) |
|---|---|
| Catalyst: | [Rh(COD)$_2$][Tf], 21 mg (0.045 mmol); (PhO)$_3$P, 29 mg (0.093 mmol) |
| Solvent: | Benzene (25 ml) |
| Reaction temp.: | 38° C. |
| Reaction time: | 10 min. |
| Conversion: | 48% |
| Yield: | 44% |

EXAMPLE 101

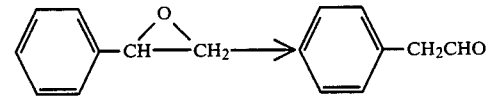

To a benzene (40 ml) solution of styrene oxide (1.20 g, 10 mmol), magnesium perchlorate (112 mg, 0.50 mmol) and triphenylphosphite (37 mg, 0.12 mmol) were added as catalysts, and the mixture was stirred at 50° C. for 10 minutes. The reaction solution was analyzed in the same manner as in Example 91, whereby it was found that the conversion of styrene oxide was 100% and the yield of phenylacetaldehyde was 63%.

EXAMPLE 102

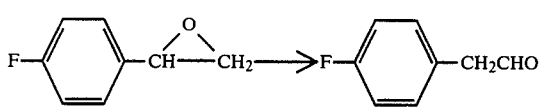

To a benzene (25 ml) solution of p-fluorostyrene oxide (691 mg, 5.0 mmol), bis(1,5-cyclooctadiene)rhodium trifluoromethanesulfonate (28 mg, 0.060 mmol) was added as a catalyst, and the mixture was stirred at 50° for 10 minutes. After cooling, the obtained reaction mixture was analyzed by an internal standard method by means of gas chromatography and the nuclear magnetic resonance spectrum, whereby it was found that the conversion of p-fluorostyrene oxide was 100% and the yield of p-fluorophenylacetaldehyde was 41%.

EXAMPLE 103

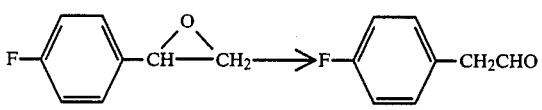

To a benzene (20 ml) solution of p-fluorostyrene oxide (0.69 g, 5.0 mmol), allyl-bis(triphenylphosphite)palladium perchlorate (19 mg, 0.022 mmol) was added as a catalyst, and the mixture was stirred at 40° C. for 10 minutes. The reaction solution was analyzed in the same manner as in Example 102, whereby it was found that the conversion of p-fluorostyrene oxide was 100% and the yield of p-fluorophenylacetaldehyde was 43%.

EXAMPLE 104

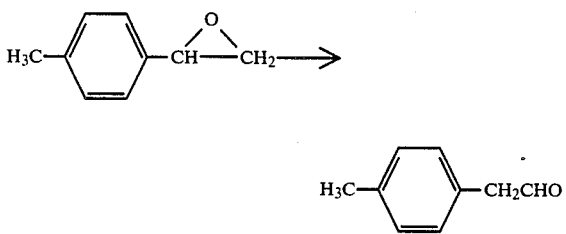

To a benzene (25 ml) solution of p-methylstyrene oxide (676 mg, 5.0 mmol), allyl-bis(triphenylphosphite)palladium perchlorate (39 mg, 0.045 mmol) was added as a catalyst, and the mixture was stirred at 50° C. for 5 minutes. After the completion of the reaction, the reaction mixture was cooled and analyzed by an internal standard method by means of gas chromatography and the nuclear magnetic resonance spectrum, whereby it was found that the conversion of p-methylstyrene oxide was 100% and the yield of p-methylphenylacetaldehyde was 31%.

EXAMPLE 105

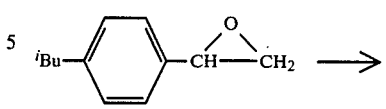

To a benzene (25 ml) solution of p-isobutylstyrene oxide (874 mg, 4.96 mmol), allyl-bis(triphenylphosphite)palladium perchlorate (20 mg, 0.023 mmol) was added as a catalyst, and the mixture was stirred at 50° C. for 5 minutes. After the completion of the reaction, the reaction mixture was cooled and analyzed by an internal standard method by means of the nuclear magnetic resonance spectrum, whereby it was found that the conversion of p-isobutylstyrene oxide was 100% and the yield of p-isobutylphenylacetaldehyde was 41%.

EXAMPLE 106

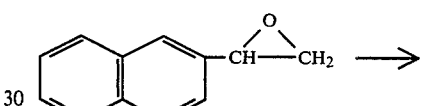

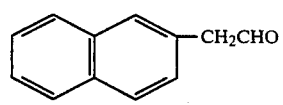

To a benzene (25 ml) solution of β-naphthylethylene oxide (850 mg, 5.0 mmol), allyl-bis(triphenylphosphite)palladium perchlorate (21 mg, 0.024 mmol) was added as a catalyst, and the mixture was stirred at 50° C. for 10 minutes. After the completion of the reaction, the reaction mixture was cooled and analyzed by an internal standard method by means of the nuclear magnetic resonance spectrum, whereby it was found that the conversion of β-naphthylethylene oxide was 100% and the yield of β-naphthylacetaldehyde was 25%.

EXAMPLE 107

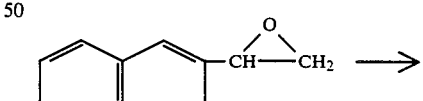

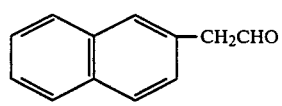

To a benzene (25 ml) solution of β-naphthylethylene oxide (852 mg, 5.0 mmol), bis(1,5-cyclooctadiene)rhodium trifluoromethanesulfonate (25 mg, 0.053 mmol) was added as a catalyst, and the mixture was stirred at 40° C. for 10 minutes. After cooling, the obtained reaction mixture was analyzed by an internal standard method by means of the nuclear magnetic resonance spectrum, whereby it was found that the conversion of β-naphthylethylene oxide was 100% and the yield of β-naphthylacetaldehyde was 26%.

EXAMPLE 108

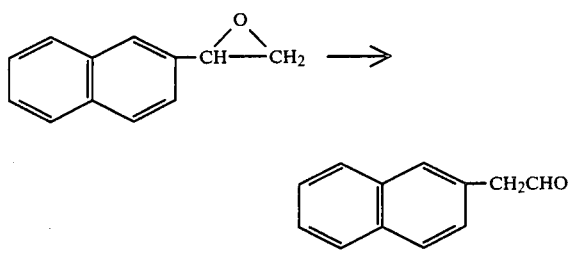

To a benzene (25 ml) solution of β-naphthylethylene oxide (851 mg, 5.0 mmol), (1,5-cyclooctadiene) bis(triphenylphosphite)rhodium trifluoromethanesulfonate (23 mg, 0.023 mmol) was added as a catalyst, whereby the reaction proceeded exothermally. The obtained reaction mixture was analyzed by an internal standard method by means of the nuclear magnetic resonance spectrum, whereby it was found that the conversion of β-naphthylethylene oxide was 100% and the yield of β-naphthylacetaldehyde was 27%.

EXAMPLE 109

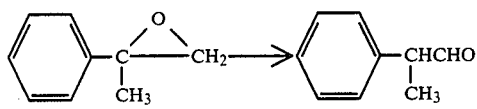

To a benzene (12.5 ml) solution of 2-phenylpropylene oxide (0.67 g, 5.0 mmol), allyl-bis(triphenylphosphite)palladium perchlorate (43 mg, 0.05 mmol) was added as a catalyst, and the mixture was stirred at 50° C. for 15 minutes. The reaction solution was analyzed in the same manner as in Example 91, whereby it was found that the conversion of 2-phenylpropylene oxide was 100% and the yield of 2-phenylpropionealdehyde was 43%.

EXAMPLE 10

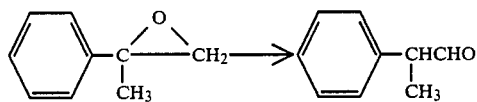

To a benzene (25 ml) solution of 2-phenylpropylene oxide (0.67 g, 5.0 mmol), magnesium perchlorate (65 mg, 0.29 mmol) and triphenylphosphite (42 mg, 0.14 mmol) were added as catalysts, and the mixture was stirred at 40° C. for 20 minutes. The reaction solution was analyzed in the same manner as in Example 91, whereby it was found that the conversion of 2-phenylpropylene oxide was 100% and the yield of 2-phenylpropionealdehyde was 67%.

The nuclear magnetic resonance spectrum data of the arylacetaldehydes obtained by the isomerization, are shown in the following table.

| | Nuclear Magnetic Resonance Spectra | |
|---|---|---|
| Example | Arylacetaldehyde | Nuclear magnetic resonance spectrum (TMS, ppm) |
| 99–101 | Phenylacetaldehyde | (CDCl$_3$) δ 3.63 (d, 2H, J = 3 Hz), 7.20 (m, 5H), 9.68 (d, 1H, J = 3 Hz) |
| 102, 103 | p-Fluorophenyl-acetaldehyde | (C$_6$D$_6$) δ 3.13 (d, 2H, J = 3 Hz), 9.12 (t, 2H) |
| 104 | p-Methylphenyl-acetaldehyde | (C$_6$D$_6$) δ 2.08 (s, 3H), 3.10 (d, 2H, J = 3 Hz), 9.32 (t, 1H, J = 3 Hz) |
| 105 | p-Isobutylphenyl-acetaldehyde | (C$_6$D$_6$) δ 0.87 (d, 6H, J = 7 Hz), 1.80 (m, 1H), 2.30 (d, 2H, J = 7 Hz), 3.12 (d, 2H, J = 3 Hz), 9.32 (t, 1H, J = 3 Hz) |
| 106–108 | β-Naphthylacet-aldehyde | (C$_6$D$_6$) δ 3.27 (d, 2H, J = 3 Hz), 9.42 (t, 1H, J = 3 Hz) |
| 109, 110 | 2-Phenylpropione-aldehyde | (CDCl$_3$) δ 1.42 (d, 3H, J = 7 Hz), 3.58 (d of q, 1H, J = 2 Hz, J = 7 Hz), 7.27 (m, 5H), 9.62 d, 1H, J = 2 Hz) |

EXAMPLE 111

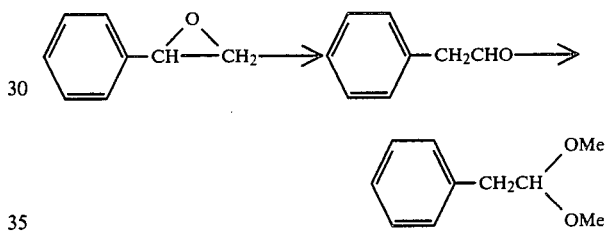

To a benzene (25 ml) solution of styrene oxide (1.20 g, 10 mmol), allyl(1,5-cyclooctadiene)palladium trifluoromethanesulfonate (41 mg, 0.10 mmol) was added as a catalyst, and the mixture was stirred at 50° C. for 10 minutes. The reaction solution was analyzed by an internal standard method by means of gas chromatography and the nuclear magnetic resonance spectrum, whereby it was found that the yield of phenylacetaldehyde was 75%. Then, to this reaction solution, methanol (10 ml) was added, and the mixture was stirred at 50° C. for 30 minutes. To the reaction mixture, a 2% sodium carbonate aqueous solution (20 ml) was added, and the organic layer and the aqueous layer were separated. The organic layer was analyzed by gas chromatography and the nuclear magnetic resonance spectrum, whereby it was found that phenylacetaldehyde disappeared completely and phenylacetaldehyde dimethylacetal formed substantially quantitatively relative to the aldehyde contained in the crude reaction mixture. The phenylacetaldehyde dimethylacetal fraction obtained by the gas chromatography, was subjected to the measurement of the nuclear magnetic resonance spectrum to determine the structure.

[$^1$H NMR(CDCl$_3$-TMS, ppm) δ2.87 (d, 2H, J=5 Hz), 3.28 (s, 6H), 4.48 (5, 1H, J=5 Hz), 7.20 (s, 5H).]

EXAMPLE 112

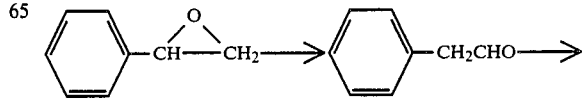

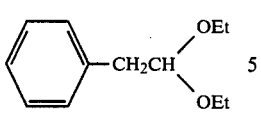

The reactions were conducted in the same manner as in Example 111 except that ethanol (10 ml) was used as the alcohol for the conversion to the acetal. The yield of phenylacetaldehyde diethylacetal was 74%.

[$^1$H NMR(CDCl$_3$-TMS, ppm) δ1.19 (t, 6H, J=7 Hz), 2.59 (d, 2H, J=6 Hz), 3.50 (q, 2H, J=7 Hz), 3.63 (q, 2H, J=7 Hz), 4.63 (t, 2H, J=6 Hz), 7.23 (s, 5H).]

EXAMPLE 113

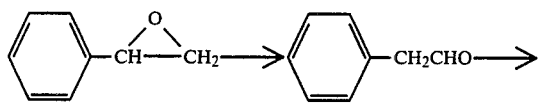

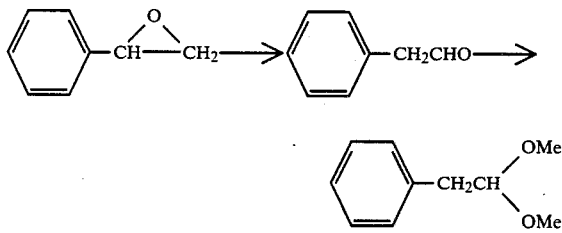

The reactions were conducted in the same manner as in Example 111 except that ethylene glycol (10 ml) was used as the alcohol for the conversion to the acetal. The yield of phenylacetaldehyde ethylene glycol acetal was 60%.

[$^1$H NMR(CDCl$_3$-TMS), ppm) δ2.90 (d, 2H, J=5 Hz), 3.82 (m, 4H), 5.00 (t, 1H, J=5 Hz), 7.20 (s, 5H).]

EXAMPLE 114

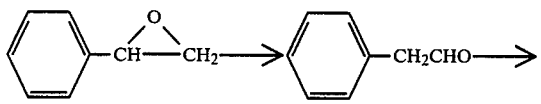

The isomerization of styrene oxide and the conversion to the acetal were conducted in the same manner as in Example 111. As the catalyst, allyl-bis(triphenylphosphite)palladium perchlorate (86 mg, 0.099 mmol) was employed, and the isomerization was conducted in a benzene (25 ml) solution at 50° C. for 5 minutes (conversion: 100%, yield: 68%). Then, the conversion to the acetal was conducted by an addition of methanol (10 ml), followed by stirring at 50° C. for 2 hours. The yield of phenylacetaldehyde acetal was quantitative relative to the aldehyde.

EXAMPLE 115

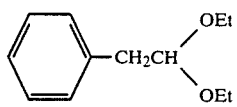

The isomerization of styrene oxide and the conversion to the acetal were conducted in the same manner as in Example 111. As the catalyst, bis(1,5-cyclooctadiene)rhodium trifluoromethanesulfonate (22 mg, 0.047 mmol) was employed, and the isomerization was conducted in a benzene (25 ml) solution at 40° C. for 10 minutes (conversion: 100%, yield: 70%). Then, the conversion to the acetal was conducted by an addition of ethanol (10 ml), followed by stirring at 45° C. for 1 hour and 30 minutes. From the analysis of the reaction solution, it was found that the yield of phenylacetaldehyde diethylacetal was substantially quantitative relative to the aldehyde.

EXAMPLE 116

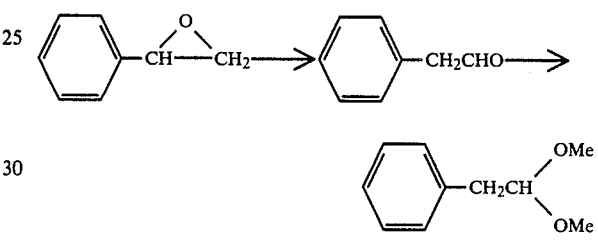

The isomerization of styrene oxide was conducted in the same manner as in Example 111. The formed phenylacetaldehyde was isolated by distillation under reduced pressure.

[Bp 60° C./5 mmHg, $^1$H NMR (CDCl$_3$-TMS, ppm) δ3.63 (d, 2H, J=3 Hz), 7.20 (m, 5H), 9.68 (d, 1H, J=3Hz).]

Then, to a benzene (15 ml) solution of the obtained phenylacetaldehyde (0.60 g, 5.0 mmol), methanol (10 ml) and allyl-bis(triphenylphosphite)palladium perchlorate (40 mg, 0.047 mmol) as a catalyst, were added, and the mixture was stirred at 40° C. for 2 hours. After cooling, a 2% sodium carbonate aqueous solution was added to the reaction solution, and the reaction solution was extracted with ether (50 ml). The organic layer was dried over sodium carbonate, and then filtered, and the solvent was distilled off, whereby colorless transparent oil (0.73 g) was obtained. From the nuclear magnetic resonance spectrum, this substance was found to be pure phenylacetaldehyde dimethylacetal. The yield was 88% relative to the phenylacetaldehyde.

EXAMPLE 117

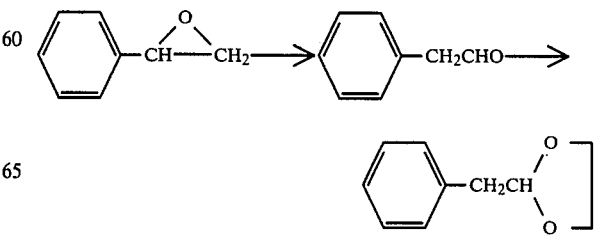

The isomerization of styrene oxide was first conducted in the same manner as in Example 116. The formed phenylacetaldehyde was isolated by distillation under reduced pressure. Then, to a benzene (15 ml) solution of the obtained phenylacetaldehyde (1.20 g, 10 mmol), ethylene glycol (5 ml) and allyl-bis(triphenylphosphite)palladium perchlorate (40 mg, 0.047 mmol) as a catalyst, were added, and the mixture was stirred at 40° C. for 2 hours. The reaction mixture was treated in the same manner as in Example 111, whereby phenylacetaldehyde ethylene glycol acetal was obtained as a colorless transparent solution (1.56 g). The yield was 95% relative to the aldehyde.

[¹H NMR (CDCl₃-TMS, ppm) δ2.90 (d, 2H, J=5 Hz), 3.82 (m, 4H), 5.00 (t, 1H, J=5 Hz), 7.20 (s, 5H).]

EXAMPLE 118

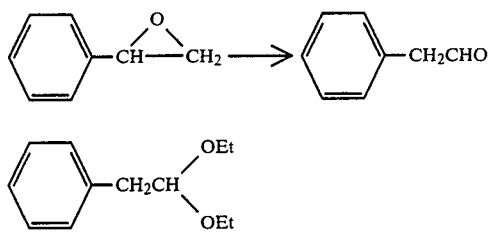

The isomerization of styrene oxide and the conversion to the acetal were conducted in the same manner as in Example 116, whereby phenylacetaldehyde diethylacetal was obtained. For the conversion to the acetal, to a benzene (15 ml) solution of phenylacetaldehyde (0.62 g, 5.0 mmol), bis(1,5-cyclooctadiene)rhodium perchlorate (40 mg, 0.085 mmol) was added as a catalyst, and ethanol (10 ml) was added. The mixture was reacted at 50° C. for 2 hours to complete the conversion to the acetal. The reaction solution was treated in the same manner, whereby a slightly yellow transparent oil (0.74 g) of phenylacetaldehyde diethylacetal was obtained. The yield was 74% relative to the aldehyde.

EXAMPLE 119

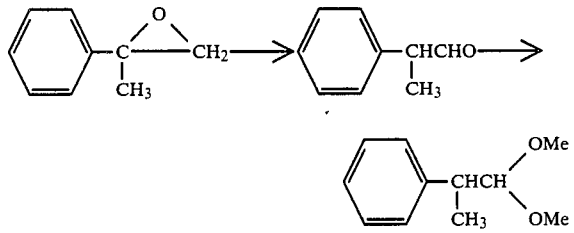

To a benzene (12.5 ml) solution of 2-phenylpropylene oxide (0.67 g, 5.0 mmol), allyl-bis(triphenylphosphite)-palladium perchlorate (43 mg, 0.05 mmol) was added as a catalyst, and the mixture was stirred at 50° C. for 15 minutes. From the analysis of the reaction solution, the yield of 2-phenylpropionealdehyde was found to be 43%. Then, methanol (10 ml) was added thereto, and the mixture was reacted at 50° C. for 1 hour. The obtained solution was treated in the same manner as in Example 111. The obtained organic layer was analyzed, whereby it was found that 2-phenylpropionealdehyde dimethylacetal formed substantially quantitatively relative to the aldehyde contained in the crude reaction mixture.

EXAMPLE 120

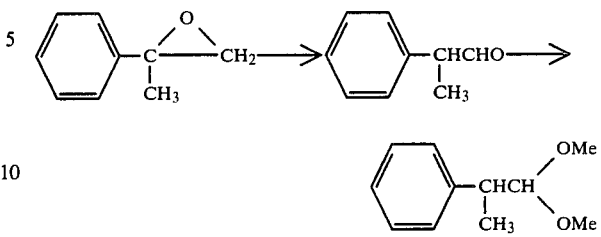

To a benzene (25 ml) solution of 2-phenylpropylene oxide (0.67 g, 5.0 mmol), magnesium perchlorate (65 mg, 0.29 mmol) and triphenylphosphite (42 mg, 0.14 mmol) were added as catalysts, and the mixture was stirred at 40° C. for 20 minutes. From the analysis of the reaction solution, the yield of 2-phenylpropionealdehyde was found to be 67%. Then, methanol (5 ml) was added thereto, and the mixture was stirred for 3 hours at a methanol refluxing temperature. The obtained reaction solution was analyzed by an internal standard method by means of gas chromatography and the nuclear magnetic resonance spectrum, whereby it was found that the aldehyde was converted to the acetal substantially quantitatively.

EXAMPLE 121

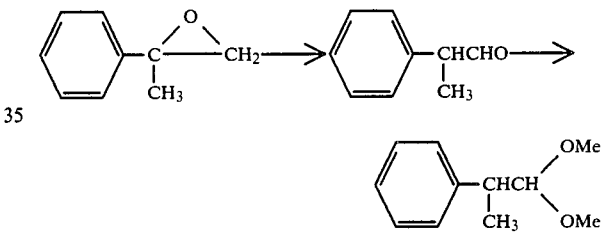

The isomerization reaction of 2-phenylpropylene oxide was conducted in the same manner as in Example 119. The formed 2-phenylpropionealdehyde was isolated by distillation under reduced pressure.

[Bp 70° C./5 mmHg, ¹H NMR (CDCl₃-TMS, ppm) δ1.42 (d, 3H, J=7 Hz), 3.58 (d of q, 1H, J=2 Hz, J=7 Hz), 7.27 (m, 5H), 9.62 (d, 1H, J=2 Hz).]

Then, to a benzene (12.5 ml) solution of the obtained 2-phenylpropionealdehyde (0.67 g, 5.0 mmol), methanol (5 ml) and allyl-bis(triphenylphosphite)palladium perchlorate (20 mg, 0.023 mmol) as a catalyst were added, and the mixture was reacted at 45° C. for 1 hour. The reaction mixture was subjected to after-treatment in the same manner as in Example 116, whereby colorless oil (0.79 g) of 2-phenylpropionealdehyde dimethylacetal was obtained. The yield was 87% relative to the aldehyde.

[¹H NMR (CDCl₃-TMS, ppm) δ2.97 (d of q, 1H, J=6 Hz, J=6 Hz), 3.20 (s, 3H), 3.33 (s, 3H), 4.32 (d, 1H, J=6 Hz), 7.23 (s, 5H).]

EXAMPLE 122

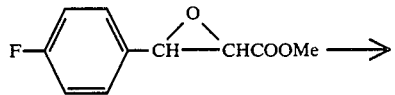

-continued

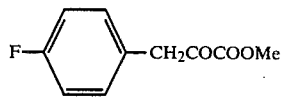

In the same manner as in Example 1, methyl 3-(4-fluorophenyl)pyruvate was obtained from methyl 3-(4-fluorophenyl)glycidate. The results are shown in the following table.

(Example 122)

| Starting material: | 2.16 g (11 mmol) |
|---|---|
| Catalyst: | [Mg][ClO$_4$]$_2$, 101 mg (0.46 mmol) |
| Solvent: | Benzene (10 ml) |
| Reaction temp.: | 80° C. |
| Reaction time: | 2 hrs. |
| Yield | 100% |

EXAMPLE 123

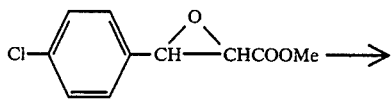

In the same manner as in Example 1, methyl 3-(4-chlorophenyl)pyruvate was obtained from methyl 3-(4-chlorophenyl)glycidate. The results are shown in the following table.

(Example 123)

| Starting material: | 2.34 g (11 mmol) |
|---|---|
| Catalyst: | [Mg][ClO$_4$]$_2$, 103 mg (0.46 mmol) |
| Solvent: | Benzene (10 ml) |
| Reaction temp.: | 80° C. |
| Reaction time: | 2 hrs. |
| Yield: | 100% |

EXAMPLE 124

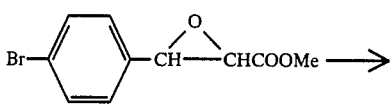

In the same manner as in Example 1, methyl 3-(4-bromophenyl)pyruvate was obtained from methyl 3-(4-bromophenyl)glycidate. The results are shown in the following table.

(Example 124)

| Starting material: | 5.14 g (20 mmol) |
|---|---|
| Catalyst: | [Mg][ClO$_4$]$_2$, 121 mg (0.54 mmol) |
| Solvent: | Benzene (20 ml) |
| Reaction temp.: | 80° C. |
| Reaction time: | 2 hrs. |
| Yield: | 100% |

EXAMPLE 125 TO 127

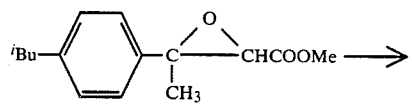

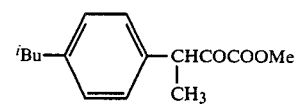

The isomerization reaction of methyl 3-methyl-(4-isobutylphenyl)glycidate was conducted in the same manner as in Example 27 except that the reaction was carried out in a sealed tube. The catalyst, the solvent and the reaction conditions are shown in the following table together with the results.

(Example 125)

| Starting material: | 1.24 g (5.0 mmol) |
|---|---|
| Catalyst: | [Zn][ClO$_4$]$_2$.6H$_2$O, 92 mg (0.25 mmol) |
| Solvent: | Toluene (10 ml) |
| Reaction temp.: | 140° C. (Bath temp.) |
| Reaction time: | 2 hrs. |
| Yield: | 100% |

(Example 126)

| Starting material: | 1.24 g (5.0 mmol) |
|---|---|
| Catalyst: | [Ag][Tf], 13 mg (0.05 mmol) |
| Solvent: | Toluene (5 ml) |
| Reaction temp.: | 140° C. (Bath temp.) |
| Reaction time: | 2 hrs. |
| Yield: | 100% |

(Example 127)

| Starting material: | 1.24 g (5.0 mmol) |
|---|---|
| Catalyst: | [Ag][ClO$_4$], 21 mg (0.1 mmol) |
| Solvent: | Benzene (5 ml) |
| Reaction temp.: | 120° C. (Bath temp) |
| Reaction time: | 2 hrs. |
| Yield: | 100% |

What is claimed is:

1. A catalyst for isomerization of a glycidate, a 2-hydroxy-3-butenoate, or an ethylene oxide derivative, consisting essentially of a salt or complex salt represented by the formula:

$$[ML_m]^{n+}[Y]_n^{-} \qquad (1)$$

where M is a metal selected from the group consisting of copper, silver, magnesium, barium, calcium, zinc, cadmium, mercury, iron, cobalt, nickel, rhodium, palladium, iridium and platinum, L is a ligand, Y is a perhalogenoate or a sulfonate, m is 0, 1, 2, 3 or 4 and n is 1, 2 or 3.

2. The catalyst according to claim 1, wherrein L is a ligand selected from the group consisting of a $\pi$-allyl group, a $\pi$-crotyl group, a $\pi$-methallyl group, a cyclopentadienyl group, an acetylacetonate group, a 8-methoxy-4-cycloocten-1-yl group, 1,5-cyclooctadiene, cyclooctatetraene, norbornadiene, dicyclopentadiene, benzene, pyridine, bipyridine, triphenylphosphine, triethylphosphine, tri-n-butylphosphine, tricyclohexylphosphine, triphenylphosphite, trimethylphosphite, triethylphosphite and tri-n-butylphosphite.

3. The catalyst according to claim 1, wherein Y is a perchlorate, a periodate, a trifluoromethanesulfonate, a fluorosulfonate, a trifluoromethylbenzenesulfonate or a methanesulfonate.

4. A method for isomerizing a glycidate, a 2-hydroxy-3-butenoate or an ethylene oxide derivative, which comprises conducting the isomerization in the presence of a salt or complex salt represented by the formula:

$$[ML_m]^{n+}[Y]_n^- \qquad (I)$$

where M is a metal selected from the group consisting of copper, silver, magnesium, barium, calcium, zinc, cadmium, mercury, iron, cobalt, nickel, rhodium, palladium, iridium and platinum, L is a ligand, Y is a perhalogenoate or a sulfonate, m is 0, 1, 2, 3 or 4 and n is 1, 2 or 3.

5. The method according to claim 6, wherein an arylglycidate represented by the formula:

$$\text{Ar}-\underset{\underset{R^1}{|}}{C}\overset{O}{\overset{/\ \ \backslash}{\phantom{X}}}\text{CHCOOR}^2 \qquad (II)$$

where Ar is an aryl group, $R^1$ is a hydrogen atom or a methyl group and $R^2$ is a lower alkyl group, is isomerized in the presence of the salt or complex salt of the formula I to form an arylpyruvate represented by the formula:

$$\text{Ar}-\underset{\underset{R^1}{|}}{CH}-\overset{O}{\overset{\|}{C}}\text{COOR}^2 \qquad (III)$$

where Ar, $R^1$ and $R^2$ are as defined above.

6. The method according to claim 6, wherein a glycidate represented by the formula:

$$\underset{\underset{R^5}{|}}{R^4-CH}\overset{R^3}{\underset{}{\diagdown}}\overset{O}{\overset{/\ \backslash}{C\text{---}C}}\overset{COOR^2}{\underset{R^6}{\diagup}} \qquad (IV)$$

where each of $R^3$, $R^4$, $R^5$ and $R^6$ is a hydrogen atom, an alkyl group, an aralkyl group or an aryl group, or $R^3$ and $R^4$, $R^3$ and $R^6$, $R^4$ and $R^5$ or $R^4$ and $R^6$ may together form a polymethylene group, and $R^2$ is a lower alkyl group, is isomerized in the presence of the salt or complex salt of the formula I to form a 2-hydroxy-3-alkenoate represented by the formula:

$$R^3-C-\underset{\underset{R^4}{\diagup}\underset{R^5}{\diagdown}}{\overset{\overset{OH}{|}}{C}}\overset{COOR^2}{\overset{/}{\diagup}}_{R^6} \qquad (V)$$

where $R^2$, $R^3$, $R^4$, $R^5$ and $R^6$ are as defined above.

7. The method according to claim 6, wherein a 2-hydroxy-3-butenoate represented by the formula:

$$\text{Ar}\diagdown\underset{\underset{CH_2}{\|}}{C}\diagup\overset{OH}{\underset{COOR^2}{}} \qquad (VI)$$

where Ar is an aryl group, and $R^2$ is a lower alkyl group, is isomerized in the presence of the salt or complex salt of the formula I to form a pyruvate represented by the formula:

$$\text{Ar}-\underset{\underset{CH_3}{|}}{CH}-\overset{O}{\overset{\|}{C}}\text{COOR}^2 \qquad (VII)$$

where Ar and $R^2$ are as defined above.

8. The method according to claim 6, wherein an ethylene oxide derivative represented by the formula:

$$\text{Ar}-\underset{\underset{R^7}{|}}{C}\overset{O}{\overset{/\ \ \backslash}{\phantom{X}}}\text{CH}_2 \qquad (VIII)$$

where Ar is an aryl group, and $R^7$ is a hydrogen atom or a lower alkyl group, is isomerized in the presence of the salt or complex salt of the formula I to form an arylacetoaldehyde represented by the formula:

$$\text{Ar}-\underset{\underset{R^7}{|}}{CH}-\text{CHO} \qquad (IX)$$

where Ar and $R^7$ are as defined above.

9. The method according to claim 10, wherein the arylacetoaldehyde of the formula IX is reacted with an alcohol represented by the formula:

$$R^8\text{OH} \qquad (X)$$

where $R^8$ is an alkyl group, in the presence of the salt or complex salt of the formula I, to form an arylacetoaldehyde acetal represented by the formula:

$$\text{Ar}-\underset{\underset{R^7}{|}}{CH}-CH\overset{OR^8}{\underset{OR^8}{\diagup\diagdown}} \qquad (XI)$$

where Ar, $R^7$ and $R^8$ are as defined above, provided that two $R^8$ may together form a substituted or unsubstituted ethylene or polymethylene group.

* * * * *